United States Patent
Ju et al.

(10) Patent No.: US 10,632,396 B2
(45) Date of Patent: Apr. 28, 2020

(54) MICROWAVE FLASH EVAPORATION PROCESS AND APPARATUS AND USE THEREOF

(71) Applicant: KUNMING UNIVERSITY OF SCIENCE AND TECHNOLOGY, Kunming, Yunnan (CN)

(72) Inventors: Shaohua Ju, Yunnan (CN); Jinhui Peng, Yunnan (CN); Zhanyong Guo, Yunnan (CN); Hua Chen, Yunnan (CN); Jun Sun, Yunnan (CN); Shenghui Guo, Yunnan (CN); Chao Liu, Yunnan (CN); Lei Xu, Yunnan (CN); Linqing Dai, Yunnan (CN); Lihua Zhang, Yunnan (CN); Shihong Tian, Yunnan (CN)

(73) Assignee: KUNMING UNIVERSITY OF SCIENCE AND TECHNOLOGY, Kunming, Yunnan (CN)

( * ) Notice: Subject to any disclaimer, the term of this patent is extended or adjusted under 35 U.S.C. 154(b) by 199 days.

(21) Appl. No.: 15/515,460

(22) PCT Filed: Apr. 19, 2016

(86) PCT No.: PCT/CN2016/079611
§ 371 (c)(1),
(2) Date: Mar. 29, 2017

(87) PCT Pub. No.: WO2016/173424
PCT Pub. Date: Nov. 3, 2016

(65) Prior Publication Data
US 2017/0225094 A1  Aug. 10, 2017

(30) Foreign Application Priority Data

Apr. 29, 2015 (CN) .......................... 2015 1 0210815
Apr. 29, 2015 (CN) .......................... 2015 1 0211058
(Continued)

(51) Int. Cl.
*B01D 1/16* (2006.01)
*B01D 1/00* (2006.01)
(Continued)

(52) U.S. Cl.
CPC .............. *B01D 1/0017* (2013.01); *A61L 2/12* (2013.01); *B01D 1/16* (2013.01); *B01D 1/20* (2013.01);
(Continued)

(58) Field of Classification Search
CPC .......... B01D 1/0017; B01D 1/16; B01D 1/20; B01D 1/305; B01D 5/006; C02F 1/06;
(Continued)

(56) References Cited

U.S. PATENT DOCUMENTS 4,313,786 A    2/1982  Smith
5,338,409 A *  8/1994  Heierli ................. B01D 1/0017
                                                      159/22
(Continued)

FOREIGN PATENT DOCUMENTS

CN    101234257 A *  8/2008  .......... B01D 1/0017
CN    201678472      12/2010
(Continued)

OTHER PUBLICATIONS

English Machine Translation of CN-101234257-A.*
(Continued)

*Primary Examiner* — Jonathan Miller
(74) *Attorney, Agent, or Firm* — Hamre, Schumann, Mueller & Larson, P.C.

(57) ABSTRACT

The present disclosure discloses a microwave flash evaporation process and apparatus and uses thereof. A microwave flash evaporation process, wherein the process makes integration of those technologies for liquid spraying, liquid droplet flash evaporation, microwave enhancement, vacuum steam discharge, and simulation and optimization of multi-mode resonant cavity, wherein through the coupling effect of the microwave, by means of one stage microwave flash evaporation, the effect normally achieved by multi-effect evaporation and flash evaporation is obtained and a liquid droplet micro-system with microwave energy transfer in situ is formed so as to prevent a circulation pump and a steam heat exchange system from being corroded under high temperature and high pressure, and prevent scaling on a heat exchanger, and improve evaporation efficiency. The present disclosure makes integration of those technologies for liquid spraying, liquid droplet flash evaporation, microwave enhancement, vacuum steam discharge, and simulation and optimization of multi-mode resonant cavity, and can be used for performing the processes of effluent disposal, seawater desalination, evaporation concentration of spent liquor of Bayer process, concentration crystallization of chemical production, sterilization of solution, unoil of solution, the rectification separation for various organic mixed solutions, sterilization, unoil and dehydration of solid powder. There is a prospect for this new process of the present disclosure with short technological process to upgrade the evaporation process.

16 Claims, 17 Drawing Sheets

(30) Foreign Application Priority Data

Apr. 29, 2015 (CN) .................... 2015 2 0268166 U
Apr. 29, 2015 (CN) .................... 2015 2 0268201 U

(51) Int. Cl.

| | |
|---|---|
| *B01D 5/00* | (2006.01) |
| *A61L 2/12* | (2006.01) |
| *B01D 1/20* | (2006.01) |
| *B01D 1/30* | (2006.01) |
| *B08B 7/00* | (2006.01) |
| *C02F 1/06* | (2006.01) |
| *C02F 1/30* | (2006.01) |
| *C02F 101/20* | (2006.01) |
| *C02F 103/08* | (2006.01) |
| *C02F 103/16* | (2006.01) |

(52) U.S. Cl.
CPC ............. *B01D 1/305* (2013.01); *B01D 5/006* (2013.01); *B08B 7/0035* (2013.01); *B08B 7/0071* (2013.01); *C02F 1/06* (2013.01); *C02F 1/302* (2013.01); *C02F 2101/20* (2013.01); *C02F 2103/08* (2013.01); *C02F 2103/16* (2013.01); *C02F 2303/04* (2013.01); *Y02A 20/128* (2018.01)

(58) Field of Classification Search
CPC .......... C02F 1/302; A61L 2/12; B08B 7/0035; B08B 7/0071
See application file for complete search history.

(56) References Cited

U.S. PATENT DOCUMENTS

| | | | | |
|---|---|---|---|---|
| 5,711,857 A | * | 1/1998 | Armstrong | B01D 1/0017 159/DIG. 26 |
| 6,303,005 B1 | * | 10/2001 | Lautenschlager | B01D 1/0011 137/386 |
| 7,119,312 B2 | * | 10/2006 | Sedlmayr | B01D 1/0017 219/688 |
| 7,332,057 B2 | * | 2/2008 | Isom | B01D 1/0017 159/44 |
| 7,665,226 B2 | * | 2/2010 | Tsuruta | A23B 4/015 219/688 |
| 10,221,079 B2 | * | 3/2019 | Ahmed | C02F 1/043 |
| 2007/0095823 A1 | * | 5/2007 | Sedlmayr | H05B 6/72 219/688 |
| 2013/0165371 A1 | * | 6/2013 | Dobry | B01J 2/04 514/5.9 |
| 2013/0228446 A1 | * | 9/2013 | Shumway | B01D 3/06 202/153 |

FOREIGN PATENT DOCUMENTS

| | | | |
|---|---|---|---|
| CN | 103127736 A | * | 6/2013 |
| CN | 103693700 | | 4/2014 |
| CN | 103964539 | | 8/2014 |
| CN | 104857734 | | 8/2015 |
| CN | 104860462 | | 8/2015 |
| CN | 204675941 | | 9/2015 |
| CN | 204767453 | | 11/2015 |
| KR | 20030021027 | | 3/2003 |
| WO | 2008104900 | | 9/2008 |

OTHER PUBLICATIONS

English Machine Translation of CN-103127736-A.*
International Search Report, issued in the corresponding PCT application No. PCT/CN2016/079611, dated Jul. 25, 2016, 6 pages.

* cited by examiner

MICROWAVE FLASH EVAPORATION PROCESS AND APPARATUS AND USE THEREOF

BACKGROUND OF THE INVENTION

Field of the Invention

The present disclosure relates to a technical filed of chemical industry, and more particular relates to a microwave flash evaporation process and apparatus, and use thereof.

Description of the Related Art

For technical field of chemical industry and metallurgy, an evaporation unit is one of operation units consuming a large amount of energy. This operation unit is widely used in those fields for seawater desalination, wastewater treatment, chemicals crystallization. As one of the important chemical operation units, evaporation unit partially evaporates water or volatile solvent contained in the solution under boiling status through heating, and then concentrates them in the concentrator. Therefore, evaporation process is a heat transfer process, and heat transfer efficiency and rate are key links of the evaporation process, for example, for the evaporation concentration of spent liquor of aluminum oxide industry, the energy consumption of evaporation takes up about 20%~25% of total energy consumption, and the cost thereof takes up about 10%~12% of total production cost. Obviously, the improvement of evaporation procedure efficiency and the reduction of energy consumption have a significant promotion effect for chemical industry and metallurgy.

At present, the evaporation apparatus includes types of single effect evaporation, multi-effect evaporation, Secondary steam contraction evaporation, multi-stage flash evaporation, and multi-stage and multi-effect flash evaporation. The type of single effect evaporation has quite low evaporation efficiency. In order to improve evaporation efficiency, the evaporation apparatus is gradually developed to the type of multi-effect evaporation. However, the multi-effect evaporation system is complex, for example, three-effect evaporation needs three pumps, three evaporation chambers, and three heat exchange systems, furthermore, those apparatus need to suffer high temperature and high pressure, and thus the cost of production is relatively high. Moreover, because the temperature of following effects is quite high so as to make the pump and valve corroded and damaged, thereby making the manufacture cost further improved. Whether multi-effect evaporation, flash evaporation, or the combination of both, there are some key poser required to be solved. First of all, the energy of evaporation mainly comes from heat exchange, and the commonly used heat resource is the type of heat exchange with steam; however, no matter whatever apparatus is used, there is a lot of heat loss. Next, the heat exchanger should suffer the high temperature and high pressure from the steam and the corrosion from material; and all of those can influence the stable operation of apparatus. Thirdly, impurity in the solution is easily to form scale on the wall surface of heat exchanger so that the heat exchange efficiency is dramatically reduced and the energy consumption is sharply raised. Fourthly, the solution flows into the flash evaporation chamber and the evaporation chamber in a form of column-like flow, and the gas-liquid interface is relatively small such that that the water molecule in the liquid column or big droplet is quite difficult to evaporate and go out due to constraint of the surrounding water molecule. Fifthly, under the condition of high vacuum degree of flash evaporation chamber and the evaporation chamber, the droplet needs more energy to evaporate the water into steam, but meanwhile, the heat convection and heat transfer is unable to pass energy to droplet. These is a vital theory and actual significance for developing a new energy saving and high efficiency evaporation technology and system with short process for metallurgy, chemical industry and environmental protection.

SUMMARY OF THE INVENTION

According to the first aspect of the present disclosure, there is provided a microwave flash evaporation process. According to the second aspect of the present disclosure, there is provided an apparatus for implementing the aforementioned microwave flash evaporation process. According to the third object of the present disclosure, there is provided the uses of the aforementioned microwave flash evaporation process.

The first aspect of the present disclosure is realize by a microwave flash evaporation process which makes integration of those technologies for liquid spraying, liquid droplet flash evaporation, microwave enhancement and vacuum steam discharge, wherein through the coupling effect of the microwave, by means of one stage microwave flash evaporation, the effect normally achieved by multi-effect evaporation and flash evaporation is obtained and a liquid droplet micro-system with microwave energy transfer in situ is formed so as to prevent a circulation pump and a steam heat exchange system from being corroded under high temperature and high pressure, and prevent scaling on a heat exchanger, and improve evaporation efficiency.

The invention can also comprise the optimization design of flash evaporation resonant cavity with microwave simulation so as to maximum the efficiency of the microwave. Firstly, the position of feed aperture can be optimized so as to solve the problem regarding uniform distribution of microwave in the cavity, resonance of the microwave, and mutual reinforce. Secondly, microwave power for each feed aperture can be optimized so as to solve the problem regarding temperature gradient distribution of an evaporation bed.

The second aspect of the invention is achieved by a microwave flash evaporation apparatus which is a microwave-evaporation apparatus, which comprises a feed tank, a liquid droplet production unit, a microwave-evaporation unit and an evaporated water recycle unit. The liquid droplet production unit comprises a feed pump, a control valve and a high pressure spray head. The microwave-evaporation unit comprises a magnetron, a demister, a thermocouple, a steam outlet, an evaporation tank, a control valve, a discharging pump, an evaporation bed, a solution outlet, a rotary shaft, a bearing and a sealing ring. The evaporated water recycle unit comprises a steam condenser, a distilled water collection tank, and a vacuum pump. An outlet of the feed tank is connected to the feed pump, the control valve and a high press spray head successively by means of pipes. The spray head is inserted into the evaporation tank from a lateral side of the evaporation tank by means of a pipe and is located at a top position inside the evaporation tank. A plurality of magnetrons are provided uniformly outside and around the evaporation tank. According to the actual conditions, a plurality of thermocouples are provided on the evaporation tank. The evaporation bed is provided just below the spray head inside the evaporation tank by means of the rotary shaft, the bearing and the sealing ring, and the evaporation bed is adjusted within a range of 0° to 90° by the rotary shaft. The solution outlet is provided at a bottom portion of evaporation tank, and is connect to two pipes, and one of the pipes is directly connected to a control valve, and the other of the pipes is connected back to the spray head by a control valve. The demister is provided at a top position inside the evaporation tank. The steam outlet is provided at a top portion of evaporation tank, and is connect to the steam condenser, the distilled water collection tank and the vacuum pump successively by means of pipes.

The present disclosure also provides another type of apparatus, wherein the feed tank is provided above the flash evaporation tank. The solution is pumped into the flash evaporation tank so as to be sprayed by means of height difference between the feed tank and the flash evaporation tank, thereby removing a pressure pump and further reducing energy consumption.

The frequency of the microwave used may be 2450±50 MHz, 915±50 MHz or 5800±50 MHz. The assembly composed of a plurality of low-power magnetrons or otherwise one or more high-power magnetrons may be used to input energy.

The third aspect of the present disclosure is achieve by the uses of the microwave flash evaporation process, wherein the microwave flash evaporation process is used for the processes of effluent disposal, seawater desalination, evaporation concentration of spent liquor of Bayer process, concentration crystallization of chemical production, sterilization of solution, unoil of solution, the rectification separation for various organic mixed solutions, sterilization, unoil and dehydration of solid powder.

Microwave is a kind of electromagnetic wave which can transfer energy in situ quickly, and also is a kind of new energy, which is green, fast, of high efficiency and easy to control. The properties of the microwave include:

Firstly, considering the difference between dielectric losses of various materials, the microwave shows the characteristic of selective heat. Considering the water molecule is a polar molecule and has a relatively large dielectric coefficient and thus a large dielectric loss, water thus has a high capacity of absorbing microwave. Secondly, the microwave has a long wavelength so that the penetration is excellent. When the microwave penetrates through the medium material, the temperature increment of the medium due to the dielectric loss causes the inner and outer of dielectric material to be heated up simultaneously so as to form a body heat source, thereby significantly reducing heat transferring time in the conventional heat.

Due to the large gas-liquid interface of the liquid droplet, the heat and mass transfer requirements are lowered for droplet evaporation and so the evaporation process is intensified. Nevertheless, the study of the droplet evaporation focuses on the liquid fuel spray combustion in car or aircraft engine cavity at home and abroad, for example, the England scholar Sazhin has summarized the development of the mode of droplet evaporation in the spray combustion. At present, the study of spray evaporation combustion focuses on the radiation effect and the convection heat exchange around the liquid droplets, mainly including the radiation effect during the droplet evaporation, the whole field numerical simulation during the droplet evaporation, and the emerging dynamics simulation of droplet evaporation. However, for concentration and crystallization process of the metallurgy and chemical industry, the flash evaporation, and falling film evaporation, rising film evaporation technology are commonly used, and the system is complex, the process is longer, and inefficient. However, the droplet evaporation hasn't been put into use yet; furthermore, the droplet evaporation action in the microwave field and numeric simulation hasn't been reported yet.

The invention aims to solve those problems such as low heat transfer efficiency, large scaling tendency, high investment cost, long technological process, and high energy consumption of the existing evaporation apparatus and process, and makes a integration of liquid spray, droplet flash evaporation, microwave field enhancement, and vacuum steam discharge so as to develop a new evaporation technology having short technological process.

The potential advantage of invention is as below:

1. make full use of the following properties or natures, such as large specific surface area of droplet, high surface free-energy and high freedom degree of the molecule at the gas-liquid interface and good wave-absorbing capacity of the droplet; make full use of the advantage of selective dehydration of the microwave so as to cause the droplet to be concentrated quickly;

2. through the coupling effect of microwave, by means of one stage microwave flash evaporation, the effect normally achieved by multi-effect evaporation and flash evaporation can be obtained, and circulation pumps and a steam heat exchange systems between various stages can be removed, and the corrosion of a circulation pump and a steam heat exchange system under high temperature and high pressure can be avoided, thereby reducing the investment cost and the operation cost;

3. Forming a liquid droplet micro-system with microwave energy transfer in situ since the chamber has a large volume and the energy required by droplet evaporation is supplied by the microwave in situ in the evaporation chamber, the scaling problem is fully avoided and heat transfer efficiency is largely increased.

System Analysis:

Droplet Increases the Specific Surface Area of the Evaporation:

make full use of the following properties or natures, such as large specific surface area of droplet, high surface free-energy and high freedom degree of the molecule at the gas-liquid interface and good wave-absorbing capacity of the droplet; make full use of the advantage of selective dehydration of the microwave so as to cause the droplet to be concentrated quickly.

Microwave Selectively Heats the Water:

The particular advantages of microwave heat: microwave can transmit in the space and cause the dielectric loss inside the material without touch, and cause the molecules of material to rotate and rub mutually such that the material can be heated quickly, and the microwave shows the advantage of body heating, selective heating and so on. Water has an excellent wave-absorbing capacity such that it can get the energy fed by the microwave so as to be heat quickly. This is quite good for the evaporated material to be heated up to the boiling point under the respective vacuum degree during the process of flash evaporation, thereby strengthening evaporation process.

In addition, the temperature inside the microwave flash evaporation chamber is controllable correctly. For the evaporation crystallization process of non-temperature-sensitive material, the temperature of chamber can raise up to several hundred centigrade. However, for the temperature-sensitive material, the temperature can be controlled to be dozens centigrade. The evaporation has a certain temperature gradient, and when droplet goes into the high temperature environment, it can absorb heat quickly and arrive the boiling point so as to evaporate the clean water out.

Evaporation System Simplification:

Through the coupling effect of microwave (or the giant power single microwave source), by means of one stage microwave flash evaporation, the effect normally achieved by multi-effect evaporation and flash evaporation can be obtained, and circulation pumps and a steam heat exchange systems between various stages can be removed, thereby significantly simplifying the apparatus and reducing the investment area and filed of the apparatus;

By Lengthening the flash evaporation chamber, plural layers of heat-absorbing plates are provided in the chamber, so as to solve the problem that stick time of droplet is short in the cavity. The temperatures of various heat-absorbing plates are designed to show a gradient increment, such that the effect of multi-stage flash evaporation is achieved in one single flash evaporation chamber.

Microwave Energy be Supplied Efficiently In Situ:

a liquid droplet micro-system with microwave energy transfer in situ is formed, so as to prevent a circulation pump and a steam heat exchange system from being corroded under high temperature and high pressure, and prevent scaling on a heat exchanger, thereby reducing operation cost and improving heat transfer efficiency.

The current energy supply for evaporation system is the type of coal-steam-heat exchanger-temperature increment of liquid to be evaporated, which renders the energy utilization rate quite low and also causes large carbon emission for impacting on the environment. There are two problems are unable to be solve in this evaporation system, (1) energy supply process and evaporation process are separated from each other, that's to say, the energy could not be supplied timely when energy is needed for evaporation; (2) energy supply obtained by steam heat exchange is restrained by the high temperature and high pressure and so on, thus tens of evaporation stages are necessary, and this makes the energy supply is limited such that evaporation efficiency is relatively low and energy consumption is relatively high.

The system in the present disclosure is the type of electric-heat-absorbing plate-absorb heat during evaporation process, and the high temperature and pressure heat exchanger is removed, the energy supply and evaporation process are implemented in one same cavity, and the energy thus could be supplied in situ when it is need for evaporation; furthermore, microwave energy supply is not restrained by temperature and pressure and so on as well as steam heat exchange, and thus the energy can fed abundantly.

The liquid can be sucked into the chamber due to both of gravity and negative pressure from the top of the chamber so that the dynamic pumps are removed and the energy consumption is decreased further.

And then, the evaporation efficiency is high and the energy consumption is low.

Performing Simulation and Optimization to Improve the Utilization Rate of the Microwave The utilization rate of the microwave may be up to 95% by combining the COMSOL and HFSS to optimize design and simulate.

The invention aims to solve those problems such as low heat transfer efficiency, large scaling tendency, high investment cost, long technological process, and high energy consumption of the existing evaporation apparatus and process, and makes a integration of liquid spray, droplet flash evaporation, microwave field enhancement, and vacuum steam discharge so as to purify the wastewater containing heavy metal ions. Through the study of this project, a new evaporation technology having short technological process is developed and there is a prospect to upgrade the evaporation process.

The energy consumption index achieved by the present disclosure is evaporated water in a range of 10~40 kilograms (Kg) per unit of electricity (KW·h), and thus the energy consumption is quite low and the problem of high energy consumption of the current apparatus and process is radically solved.

BRIEF DESCRIPTION OF THE DRAWINGS

In FIG. 1 and FIG. 2: 1—feed tank, 2—feed pump, 3—magnetron (microwave source), 4—demister, 5—thermocouple, 6—steam outlet, 7—evaporation chamber, 8—steam condenser, 9—distilled water collection tank, 10—vacuum pump, 11—control valve, 12—high pressure spray head, 13—discharging pump, 14—evaporation bed, 15—solution outlet, 16—rotary shaft, 17—bearing, 18—gasket ring;

In FIG. 5 and FIG. 6, 801—steam temperature meter, 802—steam outlet, 803—thermal insulation layer, 804—solution inlet, 805—microwave source, 806, 807—sieve plate evaporation bed, 808—droplet dispersion porous plate, 809—solution outlet, 8010—demister, 8011—concentrated solution temperature meter;

In FIG. 7 and FIG. 8: 901—steam temperature meter, 902—steam outlet, 903—thermal insulation layer, 904—demister, 905—spray head, 906—microwave source, 907—evaporation bed, 908—solution outlet, 909—concentrated solution temperature meter; 9010—solution inlet;

In FIG. 10 and FIG. 11: 101—feed tank, 102—purifier, 103—microwave source, 104—dimaster, 105—thermocouple I, 106—steam outlet, 107—high pressure spray head, 8—evaporation chamber, 109—porous wave-absorbing evaporation bed, 1010—steam condenser, 1011—distilled water collection tank, 1012—vacuum pump, 1013—control valve I, 1014—control valve II, 1015—discharge pump, 1016—concentrated solution outlet, 1017—thermocouple II, 1018—control valve III, 1019—feed pump, 1020—evaporation bed fixation table, 1021—hole;

In FIG. 13: 131—feed tank, 132—feed pump, 133—magnetron (microwave source), 134—demister, 135—thermocouple, 136—steam outlet, 137—thermal insulation layer, 138—steam condenser, 139—distilled water collection tank, 1310—vacuum pump, 1311—control valve, 1312—high pressure spray head, 1313—control valve, 1314—discharging pump, 1315—evaporation bed, 1316—thermocouple, 1317—control valve;

In FIG. 16: 161—feed tank, 162—control valve, 163—thermocouple, 164—microwave generator (microwave source), 165—primary microwave sterilization chamber, 166—thermoelement, 167—pressure regulating valve, 168—high pressure spray head, 169—secondary microwave sterilization chamber, 1610—control valve, 1611—discharging pump, 1612—control valve, 1613—feed pump;

DETAILED DESCRIPTION OF PREFERRED EMBODIMENTS OF THE INVENTION

Figure 1:
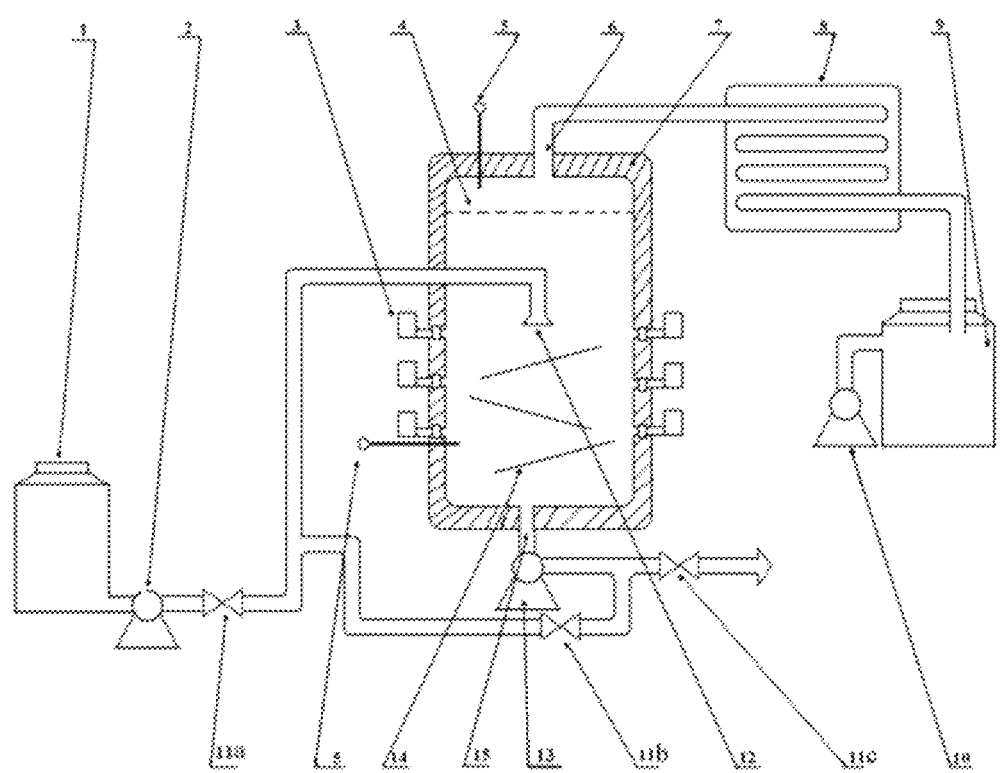
FIG. 1 is a structure schematic diagram of a microwave flash evaporation apparatus of the invention.

The present disclosure will now be described in further detail with reference to the following embodiments and the accompanying drawings, which are not to be construed as limitation to the present disclosure in any way. Any changes or substitutions based on the teachings of the present disclosure are intended to be within the scope of the present disclosure.

The present disclosure provides a microwave flash evaporation process, wherein the process makes integration of those technologies for liquid spraying, liquid droplet flash evaporation, microwave enhancement and vacuum steam discharge. Through the coupling effect of the microwave, by means of one stage microwave flash evaporation, the effect normally achieved by multi-effect evaporation and flash evaporation is obtained and a liquid droplet micro-system with microwave energy transfer in situ is formed so as to prevent a circulation pump and a steam heat exchange system from being corroded under high temperature and high pressure, and prevent scaling on a heat exchanger, and improve evaporation efficiency.

The invention also can comprise the optimization design of flash evaporation resonant cavity with microwave simulation so as to maximum the efficiency of the microwave. Firstly, the position of feed aperture can be optimized so as to solve the problem regarding uniform distribution of microwave in the cavity, resonance of the microwave, and mutual reinforce. Secondly, microwave power for each feed aperture can be optimized so as to solve the problem regarding temperature gradient distribution of an evaporation bed.

The microwave flash evaporation apparatus for implementing said process according to the present disclosure is a microwave-evaporation apparatus, which comprises a feed tank 1, a liquid droplet production unit, a microwave-evaporation unit and an evaporated water recycle unit. The liquid droplet production unit comprises a feed pump 2, a control valve 11 and a high pressure spray head 12. The microwave-evaporation unit comprises a magnetron 3, a demister 4, a thermocouple 5, a steam outlet 6, an evaporation tank 7, a control valve, a discharging pump 13, an evaporation bed 14, a solution outlet 15, a rotary shaft 16, a bearing 17 and a sealing ring 18. The evaporated water recycle unit comprises a steam condenser 8, a distilled water collection tank 9, and a vacuum pump 10. An outlet of the feed tank 1 is connected to the feed pump 2, the control valve and a high press spray head 12 successively by means of pipes. The spray head 12 is inserted into the evaporation tank 7 from a lateral side of the evaporation tank 7 by means of a pipe and is located at a top position inside the evaporation tank 7. A plurality of magnetrons 3 are provided uniformly outside and around the evaporation tank 7. According to the actual conditions, a plurality of thermocouples 5 are provided on the evaporation tank 7. The evaporation bed 14 is provided just below the spray head 12 inside the evaporation tank 7 by means of the rotary shaft 16, the bearing 17 and the sealing ring 18, and the evaporation bed 14 is adjusted within a range of 0° to 90° by the rotary shaft 16. The solution outlet 15 is provided at a bottom portion of evaporation tank 7, and is connect to two pipes, and one of the pipes is directly connected to a control valve, and the other of the pipes is connected back to the spray head 12 by a control valve. The demister 4 is provided at a top position inside the evaporation tank 7. The steam outlet 6 is provided at a top portion of evaporation tank 7, and is connect to the steam condenser 8, the distilled water collection tank 9 and the vacuum pump 10 successively by means of pipes.

The present disclosure also provides another type of apparatus, wherein the feed tank is provided above the flash evaporation tank. The solution is pumped into the flash evaporation tank so as to be sprayed by means of height difference between the feed tank and the flash evaporation tank, thereby removing a pressure pump and further reducing energy consumption.

The frequency of the microwave used may be 2450±50 MHz, 915±50 MHz or 5800±50 MHz. The assembly composed of a plurality of low-power magnetrons or otherwise one or more high-power magnetrons may be used to input energy.

A thermal insulation layer is provided between the evaporation tank 7 and the magnetron 3.

The high pressure spray head 12 is made from a reinforced plastic of modified Polytetrafluoroethylene (PTFE).

The evaporation bed 14 is made from carborundum, Silicon nitride, aluminum oxide, barium tatanate, clay soil or Wave-absorbing carbon black ceramic materials.

The evaporation tank 7 is selected from a microwave-enhanced evaporation chamber 70, a microwave fast-evaporation chamber 80 and a microwave efficient-evaporation chamber 90.

The microwave-enhanced evaporation chamber 70 comprises an evaporation cell 701, a microwave source 702, an inlet of solution to be concentrated 703, a steam outlet 704, a concentrated solution outlet 705, a demister 706 and a high pressure spray head 707. The microwave source 702 is provided at the evaporation cell 701. One end of evaporation cell 701 is provided with the steam outlet 704 the demister 706, the inlet of solution to be concentrated 703 and the high pressure spray head 707, and the other end of the evaporation cell 701 is provided with the concentrated solution outlet 705.

An inner-wall material of the evaporation cell 701 is made from a corrosion-resistant stainless steel, and is acted as a multi-mode reflector under radiation of microwave so as to make solution to be heated quickly, boiled, evaporated, and then concentrated.

A thermal insulation layer 7011 is provided at an outer-wall of the evaporation cell 701.

The thermal insulation layer 7011 is selected from thermal insulation cotton, insulation mud and thermal insulation brick.

Thermocouples are provided at an end where the steam outlet 704 of the evaporation cell 701 is located and an end where the concentrated solution outlet 705 of the evaporation cell 701 is located, connected to a microwave generator, and controlled by Micro Controller Unit (MCU) so as to adjust power of microwave in real time.

The steam outlet 704 is connected to a vacuum apparatus so as to enhance evaporation.

The microwave source 702 is provided from the end where the concentrated solution outlet 705 of the evaporation cell 701 is located to a middle position of the evaporation cell 701, and the microwave is fed into the evaporation cell 701 through a microwave feed aperture 7010 of the evaporation cell 701 so as to provide energy required by evaporation.

The microwave feed aperture 7010 is made from stainless steel flange, glass cement or Polytetrafluoroethylene gasket or quartz glass, and seal strength of the microwave feed aperture is within a range of −0.1 MPa to 1 MPa and is up to 1 MPa.

The microwave fast-evaporation chamber 80 includes a steam temperature meter 801, a steam outlet 802, a thermal insulation layer 803, a solution inlet 804, a microwave source 805, sieve plate evaporation beds 806 and 807, a droplet dispersion porous plate 808, a solution outlet 809, a demister 8010, a concentrated solution temperature meter 8011. The thermal insulation layer 803 is provided at an outer-wall of the evaporation chamber. The microwave source 805 is provided on the evaporation chamber. One end of the evaporation chamber is provided with the steam outlet 802, the steam temperature meter 801, the demister 8010 and the solution inlet 804, and the other end of the evaporation chamber is provided with the solution outlet 809, and the concentrated solution temperature meter 8011. The sieve plate evaporation beds 806, 807 and the droplet dispersion porous plate 808 are provided successively between an end where the solution outlet 809 is located and a middle portion of the evaporation chamber.

An inner-wall of the evaporation chamber 80 is made from stainless steel. After optimization design of the position of a microwave feed aperture and feeding microwave, the inner-wall of the evaporation chamber forms a multi-mode resonant cavity so as to make solution to be heated quickly, boiled, evaporated and then concentrated.

A material for making the sieve plate evaporation beds 806, 807 is wave-absorbing ceramics, and a pore diameter of the sieve plate evaporation beds 806, 807 is in the range of 0.1 mm to 20 mm.

A material for making the droplet dispersion porous plate 808 is wave-non-absorbing ceramics, and a pore diameter of the droplet dispersion porous plate 808 is in the range of 0.1 mm to 20 mm.

The microwave source 805 is provided between the end where the solution outlet 809 of the evaporation chamber is located and the middle portion of the evaporation chamber, and the microwave is fed into the evaporation chamber through a microwave feed aperture of the evaporation chamber so as to provide energy required by evaporation.

The microwave feed aperture is made from stainless steel flange, Polytetrafluoroethylene, silicone gaskets or quartz glass.

The microwave effective-evaporation chamber 90 comprises a steam temperature meter 901, a steam outlet 902, a thermal insulation layer 903, a demister 904, a high pressure spray head 905, a microwave source 906, evaporation beds 907, a solution outlet 908, a concentrated solution temperature meter 909, and a solution inlet 9010. The thermal insulation layer 903 is provided at an outer-wall of the evaporation chamber. The microwave source 906 is provided on the evaporation chamber. One end of the evaporation chamber is provided with the steam outlet 902, the steam temperature meter 901, the demister 904 and the solution inlet 9010, and an end of the solution inlet 9010 is provided with the spray head 905. The other end of the evaporation chamber is provided with the solution outlet 908, and the concentrated solution temperature meter 909. The evaporation beds 907 are provided between an end where the solution outlet 908 is located and a middle portion of the evaporation chamber.

An inner-wall of the evaporation chamber is made from stainless steel, and after optimization of the position and number of a microwave feed aperture, under the microwave, the inner-wall of the evaporation chamber forms a multi-mode resonant cavity so as to make solution to be heated quickly, boiled, evaporated and then concentrated.

The steam outlet 902 is connected to a vacuum apparatus so as to enhance evaporation.

The microwave source 906 is provided between the end where the solution outlet 908 of the evaporation chamber is located and the middle portion of the evaporation chamber, and the microwave is fed into the evaporation chamber through a microwave feed aperture of the evaporation chamber so as to provide energy required by evaporation.

The microwave feed aperture is made from stainless steel flange, glass cement, Polytetrafluoroethylene gasket or quartz glass, and seal strength of the microwave feed aperture is within a range of −0.1 MPa to 1 MPa and is up to 1 MPa.

The microwave flash evaporation process according to the present disclosure is used for the processes of effluent disposal, seawater desalination, evaporation concentration of spent liquor of Bayer process, concentration crystallization of chemical production, sterilization of solution, unoil of solution, the rectification separation for various organic mixed solutions, sterilization, unoil and dehydration of solid powder.

The effluent disposal is used for treating wastewater containing heavy metal ions, and comprises the following steps:

Step 1: pressure adjustment: adjusting pressures of an evaporation chamber and a steam condenser to be between 0.01 MPa and 0.03 Mpa by a vacuum pump;

Step 2: purification: putting the wastewater containing heavy metal ions into a feed tank, and removing big particle or agglomeration type impurity from wastewater containing heavy metal ions by a purifier in the feed tank;

Step 3: droplet and liquid film formation: passing the wastewater containing heavy metal ions through the feed pump, a high pressure spray head and then into the evaporation chamber so as to form droplets having a diameter in a range of 1 mm to 3 mm, the droplets then absorbing the microwave energy so as to concentrate during falling, and forming liquid film and droplet when arriving a porous wave-absorbing evaporation bed in the evaporation chamber;

Step 4: microwave evaporation: at the same time as step 3, turning on a microwave source of the evaporation chamber so as to directly heat the droplet and liquid film in the evaporation chamber by the microwave and at the same time indirectly heat the liquid film and the whole evaporation chamber by the microwave energy absorbed by the porous wave-absorbing evaporation bed to obtain steam;

Step 5: product collection: after passing through a demister, the steam obtained in step 4 escaping quickly from the evaporation chamber due to a negative pressure and then going into the stem condenser to be condensate, and collecting distilled water by a collection tank and obtaining concentrated solution containing heavy metal ions; and Step 6: product recycle: using the distilled water as dilution water in each stage of hydrometallurgy and wash water of boiler, directly returning the concentrated solution containing heavy metal ions to be electrolyzed so as to recycle metal ions, and recycling the metal ions in a form of hydroxide or carbonate of these heavy metal ions by using alkali to neutralize and precipitate, or recycling the metal ions in a form of metal salt crystal by secondary microwave evaporation crystallization.

The process of seawater desalination comprises the following steps:

Step 1: pressure adjustment: adjusting pressure of an evaporation chamber to be between 0.01 MPa and 0.03 Mpa by a vacuum pump;

Step 2: droplet and liquid film formation: passing the seawater through a feed pump, a high pressure spray head and then into the evaporation chamber so as to form droplet having diameter in a range of 1 mm to 3 mm, the droplet then forming a liquid film when arriving an evaporation bed;

Step 3: microwave evaporation: at the same time as step 2, turning on a microwave source around the evaporation chamber so as to heat the droplet and the liquid film in the evaporation chamber by the microwave and at the same time indirectly heat the liquid film and the whole evaporation chamber by the microwave energy absorbed by the evaporation bed to obtain steam; and Step 4: product collection: after passing through a demister, the evaporated steam escaping quickly from the evaporation chamber due to a negative pressure and then going into a stem condenser to be condensate, and collecting distilled water by a collection tank and obtaining concentrated seawater.

The seawater evaporation the evaporation concentration of spent liquor of Bayer process comprises the following steps:

Step 1: pressure adjustment: adjusting pressure of an evaporation chamber and a steam condenser to be between 0.01 MPa and 0.03 Mpa by a vacuum pump;

Step 2: droplet formation: putting the seawater or the spent liquor of Bayer process in a feed tank, then passing the seawater or the spent liquor of Bayer process through a feed pump, a high pressure spray head and then into the evaporation chamber so as to form droplet having diameter in a range of 1 mm to 3 mm;

Step 3: liquid film formation: the droplet forming a liquid film when arriving an evaporation bed in the evaporation chamber;

Step 4: microwave evaporation: at the same time as steps 2 and 3, turning on magnetrons of the evaporation chamber so as to heat the droplet and the liquid film in the evaporation chamber by the microwave and at the same time indirectly heat the liquid film and the whole evaporation chamber by the microwave energy absorbed by the evaporation bed to obtain steam; and Step 5: product collection: after passing through a demister, the steam obtained in step 4 escaping quickly from the evaporation chamber due to a negative pressure and then going into a stem condenser to be condensate, and collecting distilled water by a collection tank and obtaining concentrated seawater or concentrated spent liquor of Bayer process.

The sterilization process comprises the following steps:

Step 1: primary microwave sterilization: heating liquid up to a temperature in a range of 50° C. to 90° C. in a primary microwave sterilization chamber and sterilizing for a time in a range of 1 min to 10 min;

Step 2: secondary microwave sterilization: after the first sterilization, performing secondary microwave sterilization;

1) Pressure adjustment: adjusting pressure of a sterilization chamber to be between 0.27 MPa and 0.36 MPa by a pressure regulating valve and sterile air;

2) Liquid spray: after finishing the step 1), passing the liquid containing bacterium through a feed pump, a high pressure spray head and then into the sterilization chamber so as to form droplet having diameter in a range of 1 mm to 3 mm and uniformly distributed in the sterilization chamber; and 3) high temperature sterilization: at the same time as step 2, turning on a microwave source around the sterilization chamber so as to directly heat the droplet in the sterilization chamber by the microwave, and quickly perform sterilization by thermal effect and non-thermal effect of microwave, wherein the temperature of the sterilization chamber is control to be in a range of 130° C. to 140° C., and the sterilization time for the secondary sterilization is kept to be in a range of 0.5 s to 1.5 s; and Step 3: product collection: collecting the liquid after microwave sterilization by a collecting tank.

The process of sterilization, unoil and dehydration of solid powder comprises the following steps:

Step 1: feeding solid powder into an evaporation chamber uniformly from a top portion of the evaporation chamber;

Step 2: heating the solid powder to a set temperature by microwave;

Step 3: destroying the cytoderm of the bacterium in the solid powder by microwave electromagnetic oscillation, selectively heating and drying the cell sap by microwave so as to make the cell inactivity, and evaporating humidity and oil in the solid powder after achieving boiling point under a high vacuum condition; and Step 4: product collection: delivering the solid powder after microwave sterilization, unoil and dehydration out of the evaporation chamber and collecting it by a collecting tank.

In the following, the present disclosure will be described in further detail with reference to the specific examples.

Example 1

Figure 10:
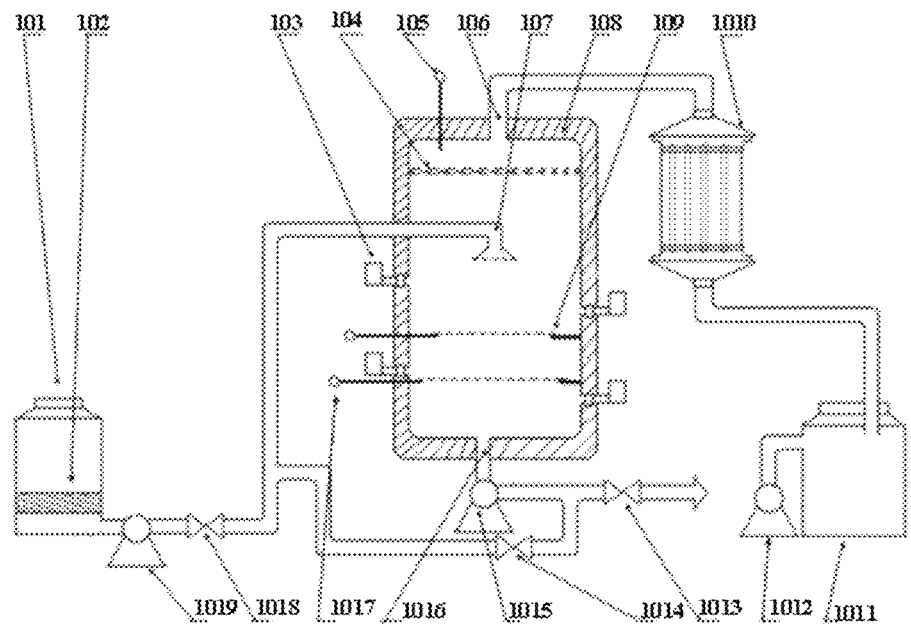
FIG. 10 is a structure schematic diagram of a microwave flash evaporation apparatus for performing effluent disposal.
Figure 11:
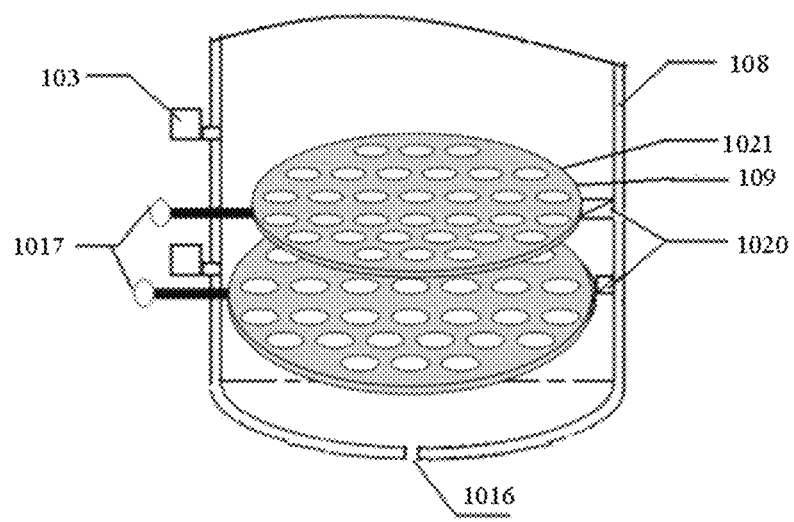
FIG. 11 is a partial structure schematic diagram of the microwave flash evaporation apparatus for performing effluent disposal.
Figure 12:
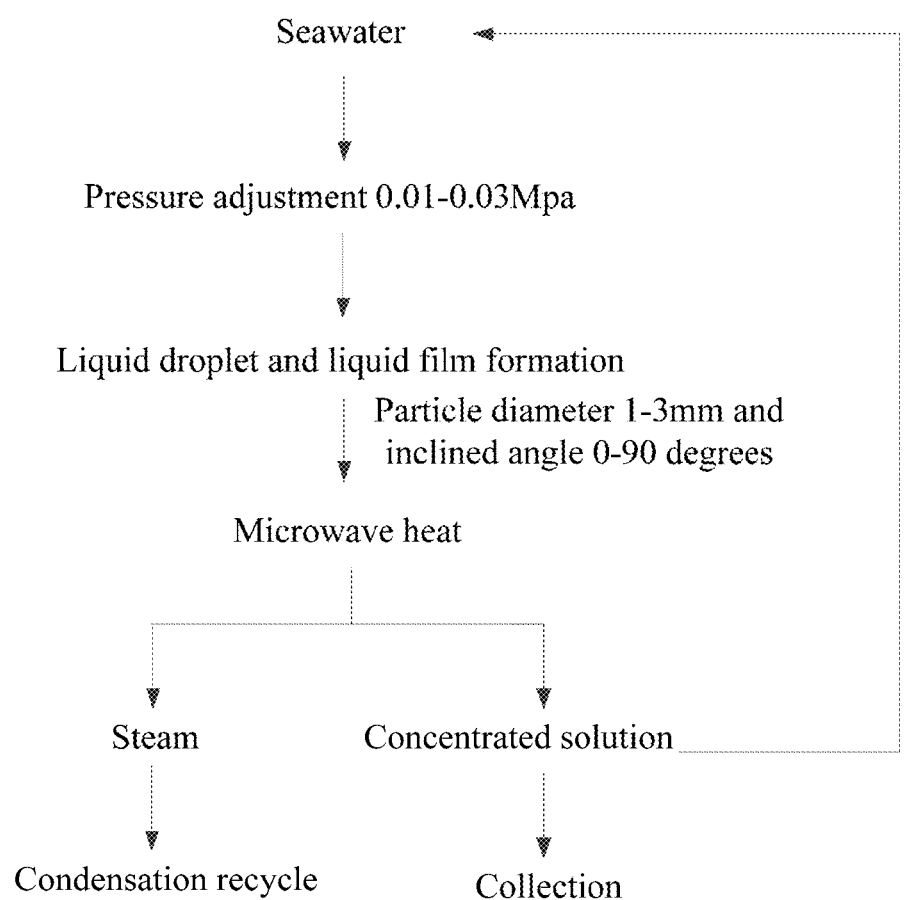
FIG. 12 is a schematic flow chart of a microwave flash evaporation process for implementing seawater desalination.

As shown in FIG. 10 and FIG. 11, the microwave purification apparatus is designed to purify the water containing heavy metal ion by using microwave, wherein the apparatus includes a feed tank 101, a purifier 102, a microwave source 103, a demister 104, thermocouples, a steam outlet 106, a high pressure spray head 107, an evaporation chamber 108, porous wave-absorbing evaporation beds 109, a steam condenser 1010, a distilled water collection tank 1011, a vacuum pump 1012, a control valve, a discharge pump 1015, a concentrated solution outlet 1016, a feed pump 1019, evaporation bed fixation tables 1020 and holes 1020. The feed tank 101 is connected to the feed pump 1019, the control valve III 1018 and then the high pressure spray head 107 successively. The purifier 102 is provided at a lower portion inside the feed tank 101. The high pressure spray head 107 enters into the evaporation chamber 108 by passing through a sidewall of the evaporation chamber 108. The steam outlet 106 and the concentrated solution outlet 1016 are provided at a top portion and a bottom portion of the evaporation chamber 108, respectively. The solution outlet 1016 is connected to the discharge pump 1015 and then is divided into two pipes after the discharge pump 1015, and one of the pipes is connected to the control valve I 1013, and the other of the pipes is connected back to the high pressure spray head 107 by the control valve II 1014. The porous wave-absorbing evaporation beds 109 are provided below the high pressure spray head 107 inside the evaporation chamber 108 by means of the evaporation bed fixation tables 1020. The surfaces of the porous wave-absorbing evaporation beds 109 are provided with a plurality of holes 1021. The demister 104 is provided at a top portion of the evaporation chamber 108. Thermocouples and microwave sources are provided around the evaporation chamber 108. The thermocouple I 105 is inserted into the top portion of the evaporation chamber 108. The thermocouples II 1017 are inserted into the evaporation chamber 108 from both sides thereof and come into contact with the porous wave-absorbing evaporation beds 109. The steam outlet 106 is connected to the steam condenser 1010, a distilled water collection tank 1011, a vacuum pump 1012 successively.

The high pressure spray head 107 is made from a reinforced plastic of modified Polytetrafluoroethylene (PTFE), which has excellent temperature resistance (−200° C. to +260° C.), corrosion resistance, aging resistance, Hydrophobic stickiness resistance and machine processability. Moreover, the PTFE is a transparent material which substantively doesn't absorb the microwave so as to ensure the uniform distribution of the microwave inside the evaporation chamber under multi-mode radiation. A thermal insulation layer is provided between the evaporation chamber 108 and the microwave source 103. The thermal insulation layer is mainly selected from thermal insulation cotton, insulation mud and thermal insulation brick. The porous wave-absorbing evaporation bed 109 is made from silicon carbide wave-absorbing ceramic material. The hole 1021 has a diameter of 1 mm.

The aforementioned microwave purification process is used for treating wastewater containing heavy metal ions, and comprises the following steps:

Step 1: pressure adjustment: adjusting pressures of the evaporation chamber 108 and the steam condenser 1010 to be 0.01 MPa by the vacuum pump 1012;

Step 2: purification: putting wastewater having a volume of 30 L containing heavy metal ions, such as $Zn^{2+}$ 1 mg/L, into the feed tank 101, and removing big sand particle from wastewater containing heavy metal ions by the purifier 102 in the feed tank 101, and preventing the big particles from blocking the high pressure spray head 107 and wearing out the pipes;

Step 3: droplet and liquid film formation: passing the wastewater containing heavy metal ions through the feed pump 1019, the high pressure spray head 107 and then into the evaporation chamber 108 so as to form droplets having a diameter of 3 mm, the droplets then absorbing the microwave energy so as to concentrate during falling, and forming liquid film and droplet when arriving a porous wave-absorbing evaporation bed 109 in the evaporation chamber 108;

Step 4: microwave evaporation: at the same time as step 3, turning on a microwave source 103 of the evaporation chamber 108 so as to directly heat the droplet and liquid film in the evaporation chamber 108 by the microwave and at the same time indirectly heat the liquid film and the whole evaporation chamber by the microwave energy absorbed by the porous wave-absorbing evaporation bed 109 to obtain steam, wherein the power of the microwave source 103 is 800 W, and the frequency thereof is 2.45 GHz;

Step 5: product collection: after passing through a demister, the steam obtained in step 4 escaping quickly from the evaporation chamber 108 due to a negative pressure and then going into the stem condenser 1010 to be condensate, and collecting distilled water by the collection tank 1011 so as to obtain the distilled water with the volume of 28.3 L and the concentrated solution containing heavy metal ions with the volume of 1.4 L, the resultant production refers to the table 1;

Step 6: product recycle: using the distilled water as dilution water in each stage of hydrometallurgy and wash water of boiler, directly returning the concentrated solution containing heavy metal ions to be electrolyzed so as to recycle metal ions, and recycling the metal ions in a form of hydroxide or carbonate of these heavy metal ions by using alkali to neutralize and precipitate, or recycling the metal ions in a form of metal salt crystal by secondary microwave evaporation crystallization.

TABLE 1

The result table of instance 1

| | Input water quality(mg/L) | Output water quality(mg/L) | Removal rate (%) | Concentration Multiples |
|---|---|---|---|---|
| $Zn^{2+}$ | 1 | non | 100 | >21 |

Example 2

As shown in FIG. 10 and FIG. 11, the microwave purification apparatus is designed to purify the water containing heavy metal ion by using microwave, wherein the apparatus includes a feed tank 101, a purifier 102, a microwave source 103, a demister 104, thermocouples, a steam outlet 106, a high pressure spray head 107, an evaporation chamber 108, porous wave-absorbing evaporation beds 109, a steam condenser 1010, a distilled water collection tank 1011, a vacuum pump 1012, a control valve, a discharge pump 1015, a concentrated solution outlet 1016, a feed pump 1019, evaporation bed fixation tables 1020 and holes 1020. The feed tank 101 is connected to the feed pump 1019, the control valve III 1018 and then the high pressure spray head 107 successively. The purifier 102 is provided at a lower portion inside the feed tank 101. The high pressure spray head 107 enters into the evaporation chamber 108 by passing through a sidewall of the evaporation chamber 108. The steam outlet 106 and the concentrated solution outlet 1016 are provided at a top portion and a bottom portion of the evaporation chamber 108, respectively. The solution outlet 1016 is connected to the discharge pump 1015 and then is divided into two pipes after the discharge pump 1015, and one of the pipes is connected to the control valve I 1013, and the other of the pipes is connected back to the high pressure spray head 107 by the control valve II 1014. The porous wave-absorbing evaporation beds 109 are provided below the high pressure spray head 107 inside the evaporation chamber 108 by means of the evaporation bed fixation tables 1020. The surfaces of the porous wave-absorbing evaporation beds 109 are provided with a plurality of holes 1021. The demister 104 is provided at a top portion of the evaporation chamber 108. Thermocouples and microwave sources are provided around the evaporation chamber 108 as required. The steam outlet 106 is connected to the steam condenser 1010, the distilled water collection tank 1011 and the vacuum pump 1012 successively.

The high pressure spray head 107 is made from a reinforced plastic of modified Polytetrafluoroethylene (PTFE), which has excellent temperature resistance (−200° C. to +260° C.), corrosion resistance, aging resistance, Hydrophobic stickiness resistance and machine processability. Moreover, the PTFE is a transparent material which substantively doesn't absorb the microwave so as to ensure the uniform distribution of the microwave inside the evaporation chamber under multi-mode radiation. A thermal insulation layer is provided between the evaporation chamber 108 and the microwave source 103. The thermal insulation layer is mainly selected from thermal insulation cotton, insulation mud and thermal insulation brick. The porous wave-absorbing evaporation bed 109 is made from silicon carbide wave-absorbing ceramic material. The hole 1021 has a diameter of 1 mm.

The aforementioned microwave purification process is used for treating wastewater containing heavy metal ions, and comprises the following steps:

Step 1: pressure adjustment: adjusting pressures of the evaporation chamber 108 and the steam condenser 1010 to be 0.03 MPa by the vacuum pump 1012;

Step 2: purification: putting wastewater having a volume of 30 L containing heavy metal ions, such as $Zn^{2+}$ 1 mg/L, $Cu^{2+}$ 1 mg/L, into the feed tank 101, and removing big sand particle and organic aggregation from wastewater containing heavy metal ions by the purifier 102 in the feed tank 101, and preventing the big particles from blocking the high pressure spray head 107 and wearing out the pipes;

Step 3: droplet and liquid film formation: passing the wastewater containing heavy metal ions through the feed pump 1019, the high pressure spray head 107 and then into the evaporation chamber 108 so as to form droplets having a diameter of 1 mm, the droplets then absorbing the microwave energy so as to concentrate during falling, and forming liquid film and droplet when arriving a porous wave-absorbing evaporation bed 109 in the evaporation chamber 108;

Step 4: microwave evaporation: at the same time as step 3, turning on a microwave source 103 of the evaporation chamber 108 so as to directly heat the droplet and liquid film in the evaporation chamber 108 by the microwave and at the same time indirectly heat the liquid film and the whole evaporation chamber by the microwave energy absorbed by the porous wave-absorbing evaporation bed 109 to obtain steam, wherein the power of the microwave source 103 is 1200 W, and the frequency thereof is 2.45 GHz;

Step 5: product collection: after passing through a demister, the steam obtained in step 4 escaping quickly from the evaporation chamber 108 due to a negative pressure and then going into the stem condenser 1010 to be condensate, and collecting distilled water by the collection tank 1011 so as to obtain the distilled water with the volume of 25.8 L and the concentrated solution containing heavy metal ions with the volume of 3.9 L, the resultant production refers to the table 102;

Step 6: product recycle: using the distilled water as dilution water in each stage of hydrometallurgy and wash water of boiler, directly returning the concentrated solution containing heavy metal ions to be electrolyzed so as to recycle metal ions, and recycling the metal ions in a form of hydroxide or carbonate of these heavy metal ions by using alkali to neutralize and precipitate, or recycling the metal ions in a form of metal salt crystal by secondary microwave evaporation crystallization.

TABLE 2

The result table of instance2

|  | Input water quality(mg/L) | Output water quality(mg/L) | Removal rate (%) | Concentration Multiples |
|---|---|---|---|---|
| $Zn^{2+}$ | 1 | non | 100 | >7 |
| $Cu^{2+}$ | 1 | non | 100 | >7 |

Example 3

As shown in FIG. 10 and FIG. 11, the microwave purification apparatus is designed to purify the water containing heavy metal ion by using microwave, wherein the apparatus includes a feed tank 101, a purifier 102, a microwave source 103, a demister 104, thermocouples, a steam outlet 106, a high pressure spray head 107, an evaporation chamber 108, porous wave-absorbing evaporation beds 109, a steam condenser 1010, a distilled water collection tank 1011, a vacuum pump 1012, a control valve, a discharge pump 1015, a concentrated solution outlet 1016, a feed pump 1019, evaporation bed fixation tables 1020 and holes 1020. The feed tank 101 is connected to the feed pump 1019, the control valve III 1018 and then the high pressure spray head 107 successively. The purifier 102 is provided at a lower portion inside the feed tank 101. The high pressure spray head 107 enters into the evaporation chamber 108 by passing through a sidewall of the evaporation chamber 108. The steam outlet 106 and the concentrated solution outlet 1016 are provided at a top portion and a bottom portion of the evaporation chamber 108, respectively. The solution outlet 1016 is connected to the discharge pump 1015 and then is divided into two pipes after the discharge pump 1015, and one of the pipes is connected to the control valve I 1013, and the other of the pipes is connected back to the high pressure spray head 107 by the control valve II 1014. The porous wave-absorbing evaporation beds 109 are provided below the high pressure spray head 107 inside the evaporation chamber 108 by means of the evaporation bed fixation tables 1020. The surfaces of the porous wave-absorbing evaporation beds 109 are provided with a plurality of holes 1021. The demister 104 is provided at a top portion of the evaporation chamber 108. Thermocouples and microwave sources are provided around the evaporation chamber 108 as required. The steam outlet 106 is connected to the steam condenser 1010, the distilled water collection tank 1011 and the vacuum pump 1012 successively.

The high pressure spray head 107 is made from a reinforced plastic of modified Polytetrafluoroethylene (PTFE), which has excellent temperature resistance (−200° C. to +260° C.), corrosion resistance, aging resistance, Hydrophobic stickiness resistance and machine processability. Moreover, the PTFE is a transparent material which substantively doesn't absorb the microwave so as to ensure the uniform distribution of the microwave inside the evaporation chamber under multi-mode radiation. A thermal insulation layer is provided between the evaporation chamber 108 and the microwave source 103. The thermal insulation layer is mainly selected from thermal insulation cotton, insulation mud and thermal insulation brick. The porous wave-absorbing evaporation bed 109 is made from silicon carbide wave-absorbing ceramic material. The hole 1021 has a diameter of 1 mm.

The aforementioned microwave purification process is used for treating wastewater containing heavy metal ions, and comprises the following steps:

Step 1: pressure adjustment: adjusting pressures of the evaporation chamber 108 and the steam condenser 1010 to be 0.03 MPa by the vacuum pump 1012;

Step 2: purification: putting wastewater having a volume of 30 L containing heavy metal ions, such as $Zn^{2+}$ 20 mg/L, $Cu^{2+}$ 20 mg/L, into the feed tank 101, and removing big sand particles and organic aggregation from wastewater containing heavy metal ions by the purifier 102 in the feed tank 101, and preventing the big particles from blocking the high pressure spray head 107 and wearing out the pipes;

Step 3: droplet and liquid film formation: passing the wastewater containing heavy metal ions through the feed pump 1019, the high pressure spray head 107 and then into the evaporation chamber 108 so as to form droplets having a diameter of 2 mm, the droplets then absorbing the microwave energy so as to concentrate during falling, and forming liquid film and droplet when arriving a porous wave-absorbing evaporation bed 109 in the evaporation chamber 108;

Step 4: microwave evaporation: at the same time as step 3, turning on a microwave source 103 of the evaporation chamber 108 so as to directly heat the droplet and liquid film in the evaporation chamber 108 by the microwave and at the same time indirectly heat the liquid film and the whole evaporation chamber by the microwave energy absorbed by the porous wave-absorbing evaporation bed 109 to obtain steam, wherein the power of the microwave source 103 is 1500 W, and the frequency thereof is 2.45 GHz;

Step 5: product collection: after passing through a demister, the steam obtained in step 4 escaping quickly from the evaporation chamber 108 due to a negative pressure and then going into the stem condenser 1010 to be condensate, and collecting distilled water by the collection tank 1011 so as to obtain the distilled water with the volume of 26.2 L and the concentrated solution containing heavy metal ions with the volume of 3.6 L, the resultant production refers to the table 3; Step 6: product recycle: using the distilled water as dilution water in each stage of hydrometallurgy and wash water of boiler, directly returning the concentrated solution containing heavy metal ions to be electrolyzed so as to recycle metal ions, and recycling the metal ions in a form of hydroxide or carbonate of these heavy metal ions by using alkali to neutralize and precipitate, or recycling the metal ions in a form of metal salt crystal by secondary microwave evaporation crystallization.

TABLE 3

The result table of instance 3

|  | Input water quality(mg/L) | Output water quality(mg/L) | Removal rate (%) | Concentration Multiples |
|---|---|---|---|---|
| $Zn^{2+}$ | 20 | 0.13 | 99.3 | >166 |
| $Cu^{2+}$ | 20 | 0.13 | 99.3 | >166 |

Example 4

As shown in FIG. 10 and FIG. 11, the microwave purification apparatus is designed to purify the water containing heavy metal ion by using microwave, wherein the apparatus includes a feed tank 101, a purifier 102, a microwave source 103, a demister 104, thermocouples, a steam outlet 106, a high pressure spray head 107, an evaporation chamber 108, porous wave-absorbing evaporation beds 109, a steam condenser 1010, a distilled water collection tank 1011, a vacuum pump 1012, a control valve, a discharge pump 1015, a concentrated solution outlet 1016, a feed pump 1019, evaporation bed fixation tables 1020 and holes 1020. The feed tank 101 is connected to the feed pump 1019, the control valve III 1018 and then the high pressure spray head 107 successively. The purifier 102 is provided at a lower portion inside the feed tank 101. The high pressure spray head 107 enters into the evaporation chamber 108 by passing through a sidewall of the evaporation chamber 108. The steam outlet 106 and the concentrated solution outlet 1016 are provided at a top portion and a bottom portion of the evaporation chamber 108, respectively. The solution outlet 1016 is connected to the discharge pump 1015 and then is divided into two pipes after the discharge pump 1015, and one of the pipes is connected to the control valve I 1013, and the other of the pipes is connected back to the high pressure spray head 107 by the control valve II 1014. The porous wave-absorbing evaporation beds 109 are provided below the high pressure spray head 107 inside the evaporation chamber 108 by means of the evaporation bed fixation tables 1020. The surfaces of the porous wave-absorbing evaporation beds 109 are provided with a plurality of holes 1021. The demister 104 is provided at a top portion of the evaporation chamber 108. Thermocouples and microwave sources 103 are provided around the evaporation chamber 108 as required. The steam outlet 106 is connected to the steam condenser 1010, the distilled water collection tank 1011 and the vacuum pump 1012 successively.

The high pressure spray head 107 is made from a reinforced plastic of modified Polytetrafluoroethylene (PTFE), which has excellent temperature resistance (−200° C. to +260° C.), corrosion resistance, aging resistance, Hydrophobic stickiness resistance and machine processability. Moreover, the PTFE is a transparent material which substantively doesn't absorb the microwave so as to ensure the uniform distribution of the microwave inside the evaporation chamber under multi-mode radiation. A thermal insulation layer is provided between the evaporation chamber 108 and the microwave source 103. The thermal insulation layer is mainly selected from thermal insulation cotton, insulation mud and thermal insulation brick. The porous wave-absorbing evaporation bed 109 is made from silicon carbide wave-absorbing ceramic material. The hole 1021 has a diameter of 1 mm.

The aforementioned microwave purification process is used for treating wastewater containing heavy metal ions, and comprises the following steps:

Step 1: pressure adjustment: adjusting pressures of the evaporation chamber 108 and the steam condenser 1010 to be 0.02 MPa by the vacuum pump 1012;

Step 2: purification: putting wastewater having a volume of 30 L containing heavy metal ions, such as $Zn^{2+}$ 10 mg/L, $Mg^{2+}$ 20 mg/L, $Cu^{2+}$ 20 mg/L, into the feed tank 101, and removing big particle and organic impurity from wastewater containing heavy metal ions by the purifier 102 in the feed tank 101, and preventing the big particles from blocking the high pressure spray head 107 and wearing out the pipes;

Step 3: droplet and liquid film formation: passing the wastewater containing heavy metal ions through the feed pump 1019, the high pressure spray head 107 and then into the evaporation chamber 108 so as to form droplets having a diameter of 3 mm, the droplets then absorbing the microwave energy so as to concentrate during falling, and forming liquid film and droplet when arriving a porous wave-absorbing evaporation bed 109 in the evaporation chamber 108;

Step 4: microwave evaporation: at the same time as step 3, turning on a microwave source 103 of the evaporation chamber 108 so as to directly heat the droplet and liquid film in the evaporation chamber 108 by the microwave and at the same time indirectly heat the liquid film and the whole evaporation chamber by the microwave energy absorbed by the porous wave-absorbing evaporation bed 109 to obtain steam, wherein the power of the microwave source 103 is 1500 W, and the frequency thereof is 2.45 GHz;

Step 5: product collection: after passing through a demister, the steam obtained in step 4 escaping quickly from the evaporation chamber 108 due to a negative pressure and then going into the stem condenser 1010 to be condensate, and collecting distilled water by the collection tank 1011 so as to obtain the distilled water with the volume of 26.4 L and the concentrated solution containing heavy metal ions with the volume of 2.5 L, the resultant production refers to the table 4;

Step 6: product recycle: using the distilled water as dilution water in each stage of hydrometallurgy and wash water of boiler, directly returning the concentrated solution containing heavy metal ions to be electrolyzed so as to recycle metal ions, and recycling the metal ions in a form of hydroxide or carbonate of these heavy metal ions by using alkali to neutralize and precipitate, or recycling the metal ions in a form of metal salt crystal by secondary microwave evaporation crystallization.

TABLE 4

The result table of instance 4

| | Input water quality(mg/L) | Output water quality(mg/L) | Removal rate (%) | Concentration Multiples |
|---|---|---|---|---|
| $Zn^{2+}$ | 10 | 0.05 | 99.5 | >120 |
| $Mg^{2+}$ | 20 | 0.11 | 99.4 | >240 |
| $Cu^{2+}$ | 20 | 0.14 | 99.3 | >240 |

Example 5

Figure 13:
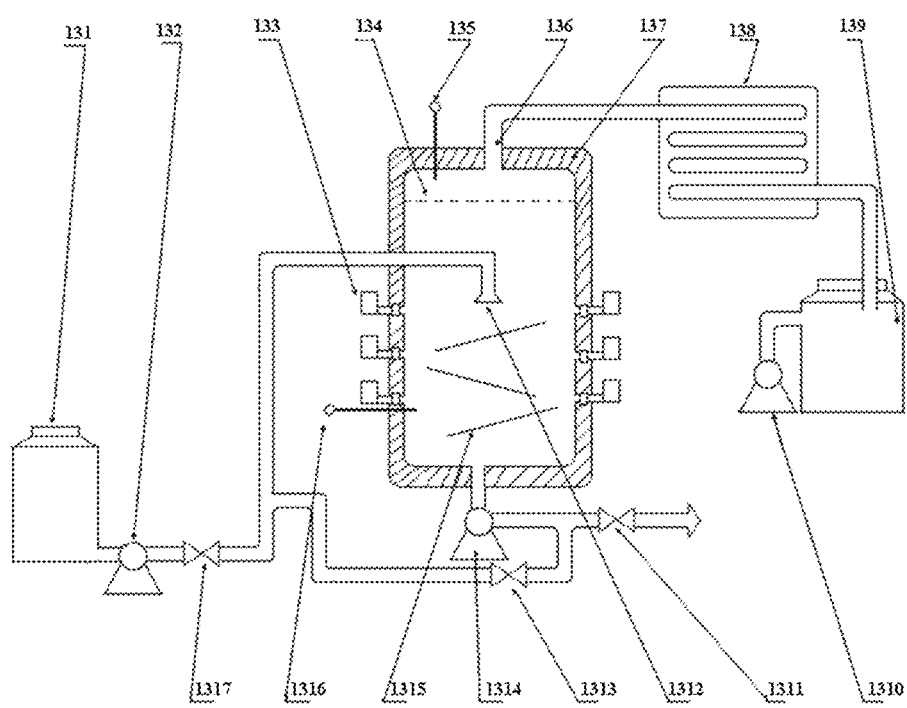
FIG. 13 is a structure schematic diagram of a microwave flash evaporation apparatus for performing seawater desalination.
Figure 14:
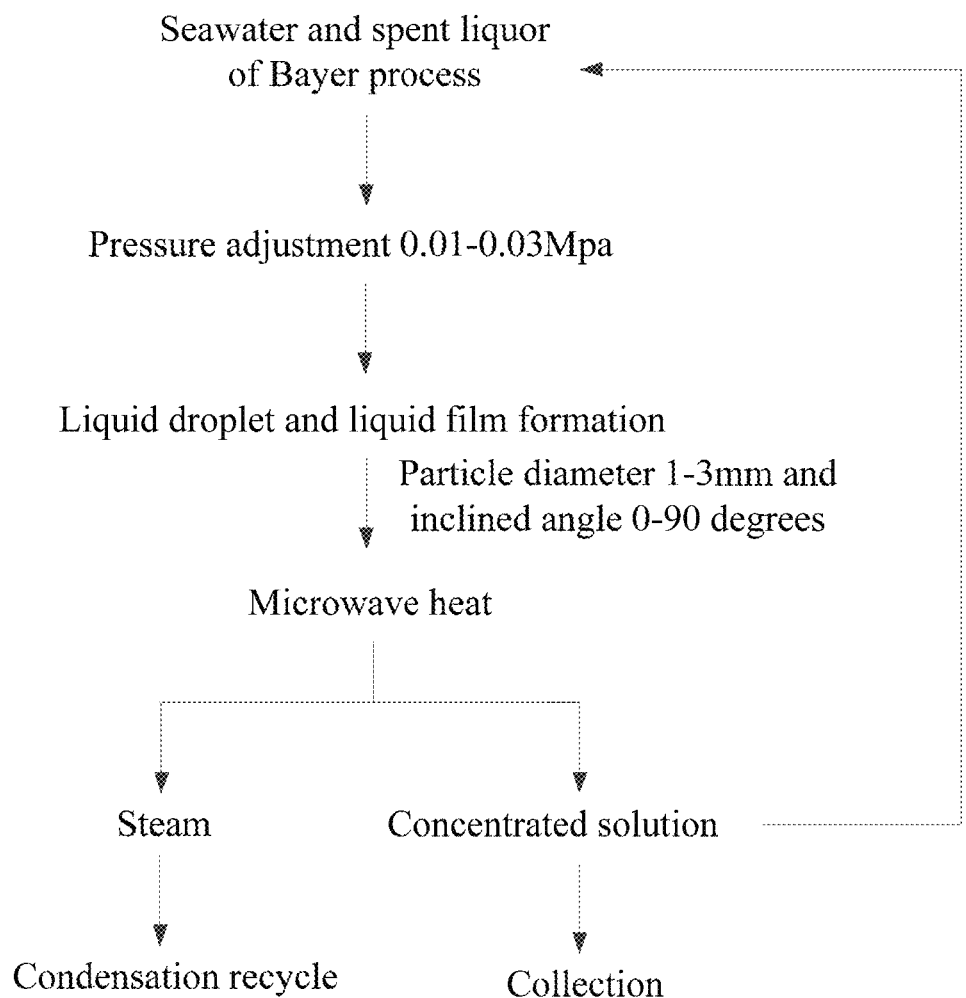
FIG. 14 is a schematic flow chart of a microwave flash evaporation process for implementing seawater evaporation or evaporation concentration of spent liquor of Bayer process.
Figure 15:
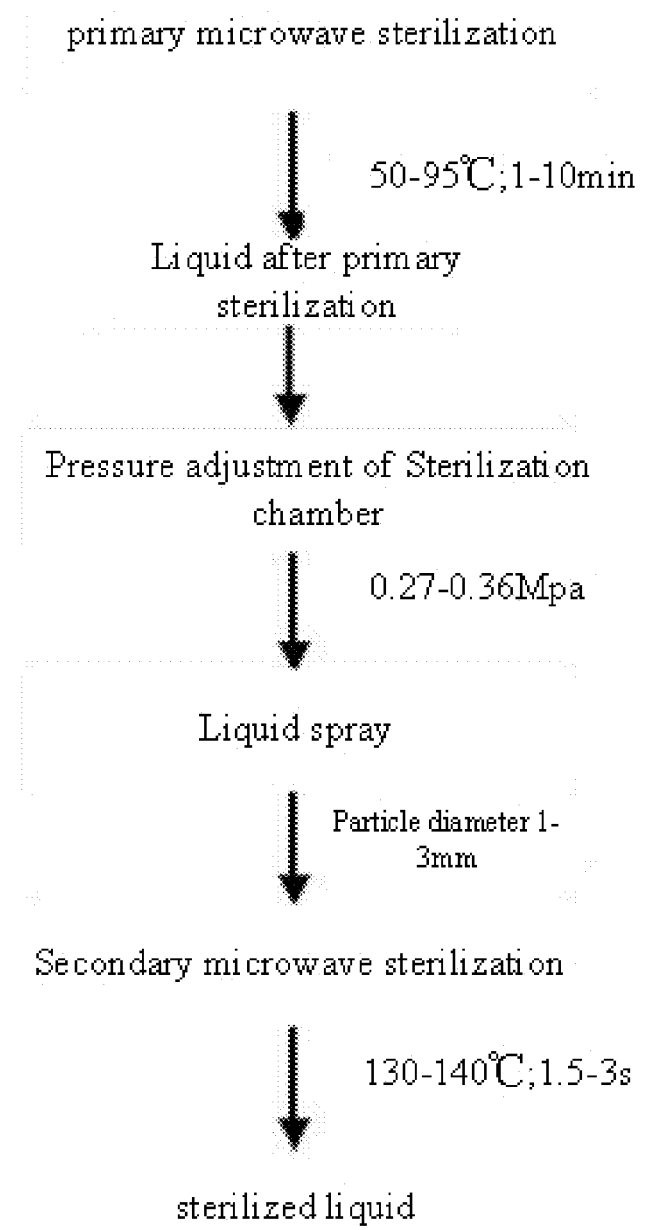
FIG. 15 is a schematic flow chart of a microwave flash evaporation process for implementing sterilization.
Figure 16:
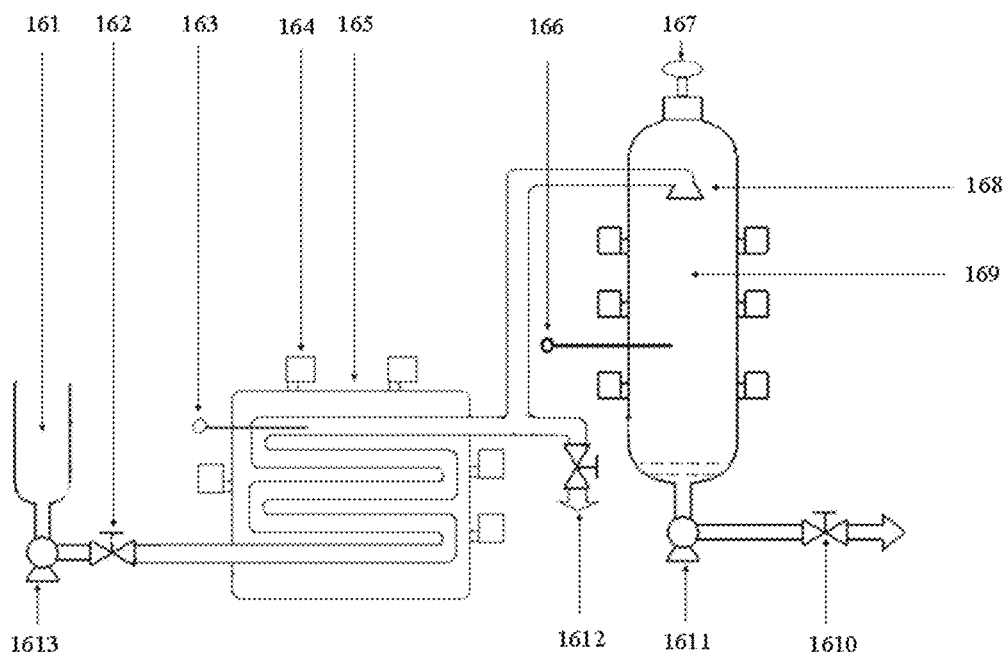
FIG. 16 is a schematic structure diagram of a microwave flash evaporation apparatus for implementing sterilization.
Figure 17:
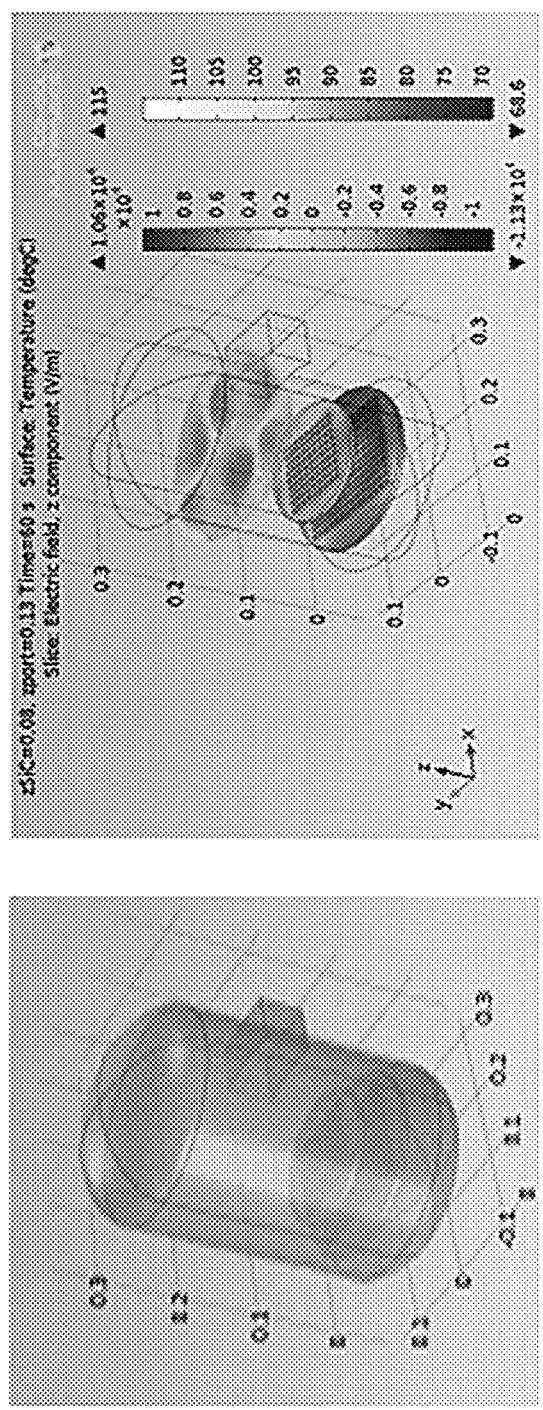
FIG. 17 is an optimization simulation of multi-mode microwave flash evaporation resonant cavity, wherein SiC ceramic plate is heated by a single feed aperture microwave.
Figure 18:
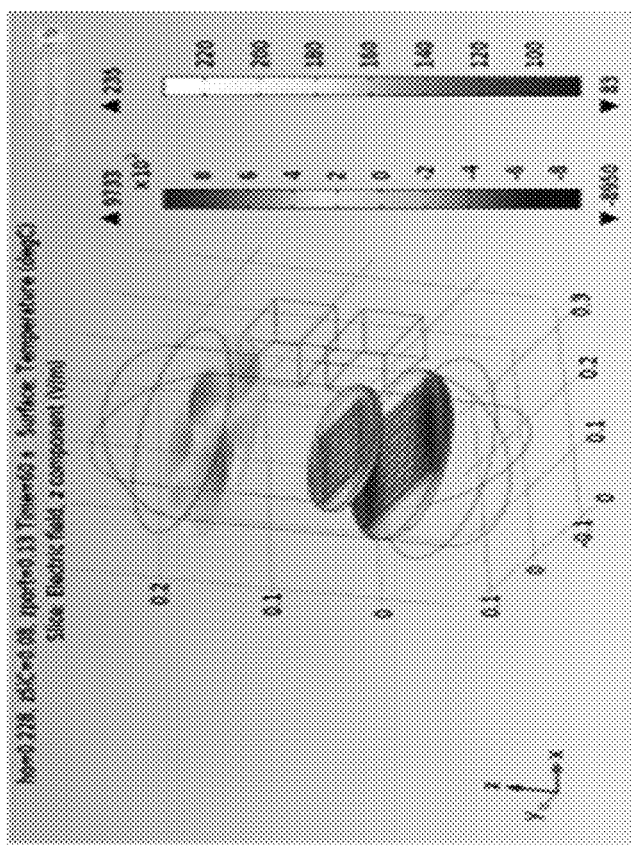
FIG. 18 is an optimization simulation of multi-mode microwave flash evaporation resonant cavity with double feed apertures.
Figure 18:
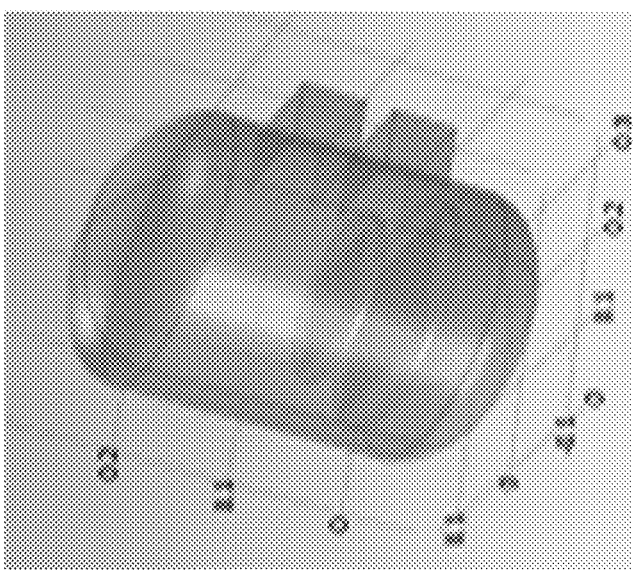
Figure 19:
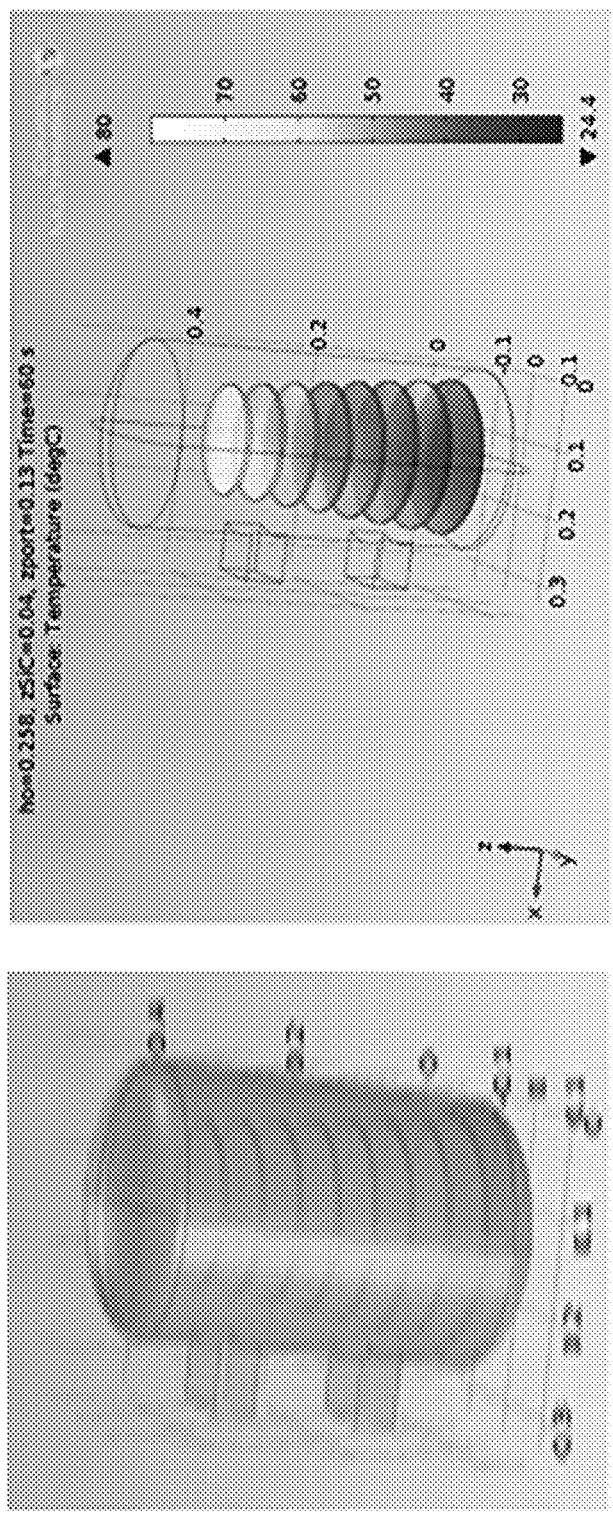
FIG. 19 is an optimization simulation of multi-mode microwave flash evaporation resonant cavity with double feed apertures and a plurality of evaporation beds.

As shown in FIG. 13, FIG. 13 shows an efficient and energy-saving microwave evaporation process and apparatus for performing seawater desalination, the apparatus comprises a feed tank 131, a feed pump 132, magnetrons 133, a demister 134, thermocouples 135, a steam outlet 136, a thermal insulation layer 137, a steam condenser 138, a distilled water collection tank 139, a vacuum pump 1310, a high pressure spray head 1312, a discharge pump 1314, evaporation beds 1315, connection pipes and control valves 1311,1313,1317. The seawater desalination process comprises the following steps:

Step 1: pressure adjustment: adjusting pressure of the evaporation chamber to be 0.01 MPa by the vacuum pump;

Step 2: droplet and liquid film formation: passing the seawater having a volume of 30 L through the feed pump, the high pressure spray head and then into the evaporation chamber so as to form droplet having diameter of 3 mm, the droplet then forming a liquid film when arriving the evaporation bed having an inclined angle with respect to a horizontal direction of 0 degree;

Step 3: microwave evaporation: at the same time as step 2, turning on a microwave source around the evaporation chamber so as to heat the droplet and the liquid film in the evaporation chamber by the microwave and at the same time indirectly heat the liquid film and the whole evaporation chamber by the microwave energy absorbed by the evaporation bed to obtain steam, wherein the power of the microwave source 133 is 600 W, and the frequency thereof is 2.45 GHz; and Step 4: product collection: after passing through a demister, the evaporated steam escaping quickly from the evaporation chamber due to a negative pressure and then going into a stem condenser to be condensate, and collecting distilled water by a collection tank and obtaining concentrated seawater.

The distilled water with a volume of 29 L may be collected through the abovementioned process.

Example 6

As shown in FIG. 13, FIG. 13 shows an efficient and energy-saving microwave evaporation process and apparatus for performing seawater desalination, the apparatus comprises a feed tank 131, a feed pump 132, magnetrons 133, a demister 134, thermocouples 135, a steam outlet 136, a thermal insulation layer 137, a steam condenser 138, a distilled water collection tank 139, a vacuum pump 1310, a high pressure spray head 1312, a discharge pump 1314, evaporation beds 1315, connection pipes and control valves 1311, 1313, 1317. The seawater desalination process comprises the following steps:

Step 1: pressure adjustment: adjusting pressure of the evaporation chamber to be 0.03 MPa by the vacuum pump;

Step 2: droplet and liquid film formation: passing the seawater having a volume of 30 L through the feed pump, the high pressure spray head and then into the evaporation chamber so as to form droplet having diameter of 1 mm, the droplet then forming a liquid film when arriving the evaporation bed having an inclined angle with respect to a horizontal direction of 45 degree;

Step 3: microwave evaporation: at the same time as step 2, turning on a microwave source around the evaporation chamber so as to heat the droplet and the liquid film in the evaporation chamber by the microwave and at the same time indirectly heat the liquid film and the whole evaporation chamber by the microwave energy absorbed by the evaporation bed to obtain steam, wherein the power of the microwave source 133 is 800 W, and the frequency thereof is 2.45 GHz; and Step 4: product collection: after passing through a demister, the evaporated steam escaping quickly from the evaporation chamber due to a negative pressure and then going into a stem condenser to be condensate, and collecting distilled water by a collection tank and obtaining concentrated seawater.

The distilled water with a volume of 27.7 L may be collected through the abovementioned process.

Example 7

As shown in FIG. 13, FIG. 13 shows an efficient and energy-saving microwave evaporation process and apparatus for performing seawater desalination, the apparatus comprises a feed tank 131, a feed pump 132, magnetrons 133, a demister 134, thermocouples 135, a steam outlet 136, a thermal insulation layer 137, a steam condenser 138, a distilled water collection tank 139, a vacuum pump 1310, a high pressure spray head 1312, a discharge pump 1314, evaporation beds 1315, connection pipes and control valves 1311, 1313, 1317. The seawater desalination process comprises the following steps:

Step 1: pressure adjustment: adjusting pressure of the evaporation chamber to be 0.03 MPa by the vacuum pump;

Step 2: droplet and liquid film formation: passing the seawater having a volume of 30 L through the feed pump, the high pressure spray head and then into the evaporation chamber so as to form droplet having diameter of 3 mm, the droplet then forming a liquid film when arriving the evaporation bed having an inclined angle with respect to a horizontal direction of 90 degree;

Step 3: microwave evaporation: at the same time as step 2, turning on a microwave source around the evaporation chamber so as to heat the droplet and the liquid film in the evaporation chamber by the microwave and at the same time indirectly heat the liquid film and the whole evaporation chamber by the microwave energy absorbed by the evaporation bed to obtain steam, wherein the power of the microwave source 133 is 1200 W, and the frequency thereof is 2.45 GHz; and Step 4: product collection: after passing through a demister, the evaporated steam escaping quickly from the evaporation chamber due to a negative pressure and then going into a stem condenser to be condensate, and collecting distilled water by a collection tank and obtaining concentrated seawater.

The distilled water with a volume of 25.5 L may be collected through the abovementioned process.

Example 8

As shown in FIG. 13, FIG. 13 shows an efficient and energy-saving microwave evaporation process and apparatus for performing seawater desalination, the apparatus comprises a feed tank 131, a feed pump 132, magnetrons 133, a demister 134, thermocouples 135, a steam outlet 136, a thermal insulation layer 137, a steam condenser 138, a distilled water collection tank 139, a vacuum pump 1310, a high pressure spray head 1312, a discharge pump 1314, evaporation beds 1315, connection pipes and control valves 1311, 1313, 1317. The seawater desalination process comprises the following steps:

Step 1: pressure adjustment: adjusting pressure of the evaporation chamber to be 0.02 MPa by the vacuum pump;

Step 2: droplet and liquid film formation: passing the seawater having a volume of 300 L through the feed pump, the high pressure spray head and then into the evaporation chamber so as to form droplet having diameter of 1 mm, the droplet then forming a liquid film when arriving the evaporation bed having an inclined angle with respect to a horizontal direction of 10 degree;

Step 3: microwave evaporation: at the same time as step 2, turning on a microwave source around the evaporation chamber so as to heat the droplet and the liquid film in the evaporation chamber by the microwave and at the same time indirectly heat the liquid film and the whole evaporation chamber by the microwave energy absorbed by the evaporation bed to obtain steam, wherein the power of the microwave source 133 is 10 kW, and the frequency thereof is 2.45 GHz; and Step 4: product collection: after passing through a demister, the evaporated steam escaping quickly from the evaporation chamber due to a negative pressure and then going into a stem condenser to be condensate, and collecting distilled water by a collection tank and obtaining concentrated seawater.

The distilled water with a volume of 278 L may be collected through the abovementioned process.

Example 9

As shown in FIG. 13, FIG. 13 shows an efficient and energy-saving microwave evaporation process and apparatus for performing seawater desalination, the apparatus comprises a feed tank 131, a feed pump 132, magnetrons 133, a demister 134, thermocouples 135, a steam outlet 136, a thermal insulation layer 137, a steam condenser 138, a distilled water collection tank 139, a vacuum pump 1310, a high pressure spray head 1312, a discharge pump 1314, evaporation beds 1315, connection pipes and control valves 1311, 1313, 1317. The seawater desalination process comprises the following steps:

Step 1: pressure adjustment: adjusting pressure of the evaporation chamber to be 0.01 MPa by the vacuum pump;

Step 2: droplet and liquid film formation: passing the seawater having a volume of 300 L through the feed pump, the high pressure spray head and then into the evaporation chamber so as to form droplet having diameter of 1 mm, the droplet then forming a liquid film when arriving the evaporation bed having an inclined angle with respect to a horizontal direction of 20 degree;

Step 3: microwave evaporation: at the same time as step 2, turning on a microwave source around the evaporation chamber so as to heat the droplet and the liquid film in the evaporation chamber by the microwave and at the same time indirectly heat the liquid film and the whole evaporation chamber by the microwave energy absorbed by the evaporation bed to obtain steam, wherein the power of the microwave source 133 is 25 kW, and the frequency thereof is 2.45 GHz; and Step 4: product collection: after passing through a demister, the evaporated steam escaping quickly from the evaporation chamber due to a negative pressure and then going into a stem condenser to be condensate, and collecting distilled water by a collection tank and obtaining concentrated seawater.

The distilled water with a volume of 296 L may be collected through the abovementioned process.

Example 10

Figure 2:
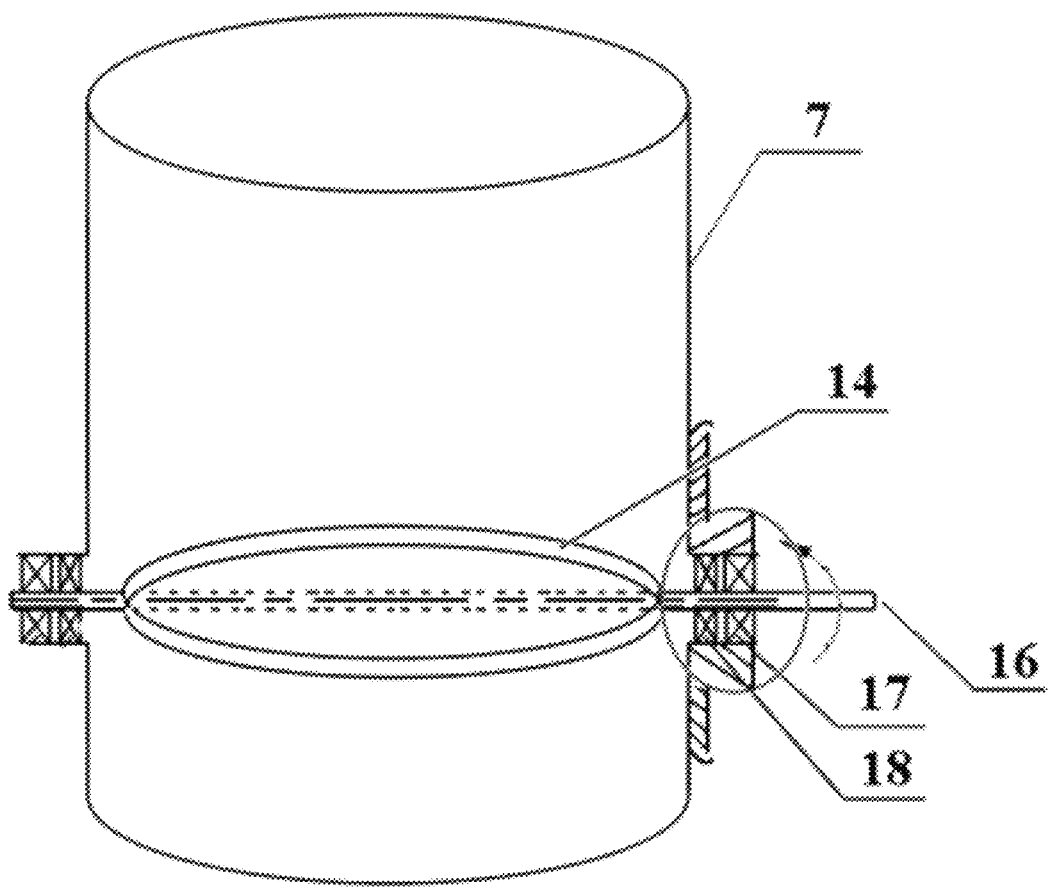
FIG. 2 is a structure schematic diagram of an evaporation tank of the microwave flash evaporation apparatus of the invention.
Figure 3:
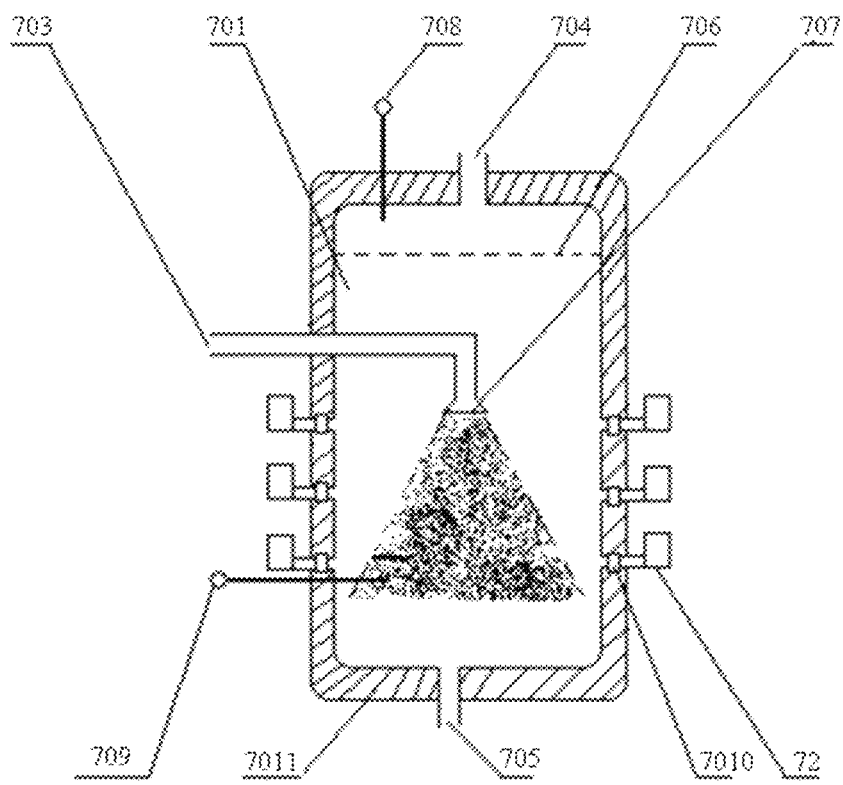
FIG. 3 is a structure schematic diagram of a microwave-enhanced evaporation chamber.
Figure 4:
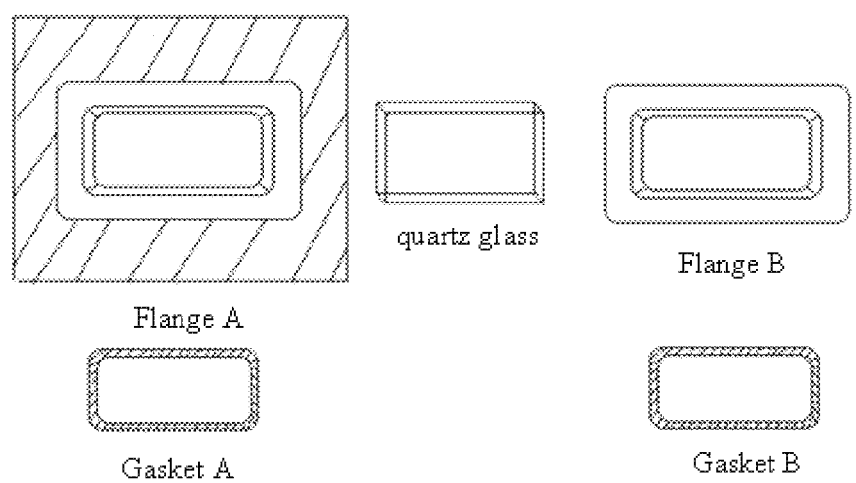
FIG. 4 is a structure schematic diagram of a microwave feed aperture of the microwave-enhanced evaporation chamber In FIG. 3 and FIG. 4 701—evaporation cell, 702—microwave source, 703—inlet of solution to be concentrated, 704—steam outlet, 705—concentrated solution outlet, 706—demister, 707—high pressure spray head, 708, 709—thermocouple, 7010—quartz glass, 7011—thermal insulation layer.
Figure 5:
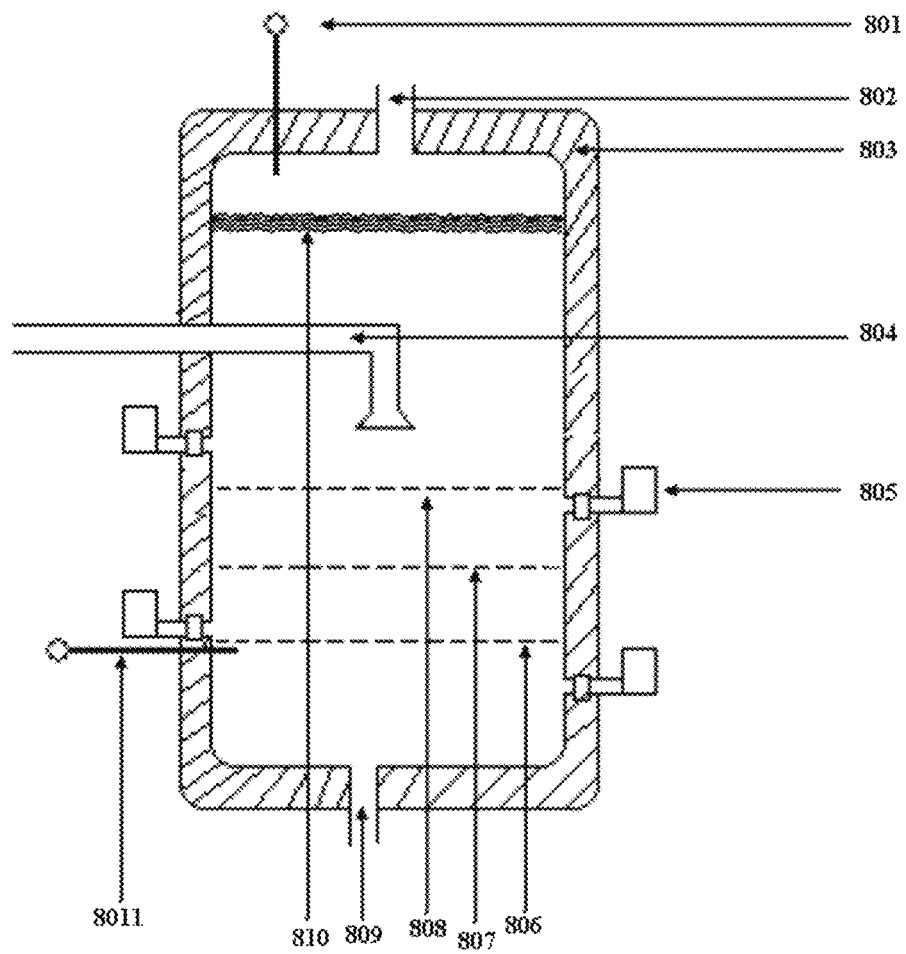
FIG. 5 is a structure schematic diagram of a microwave fast-evaporation chamber of the invention.
Figure 6:
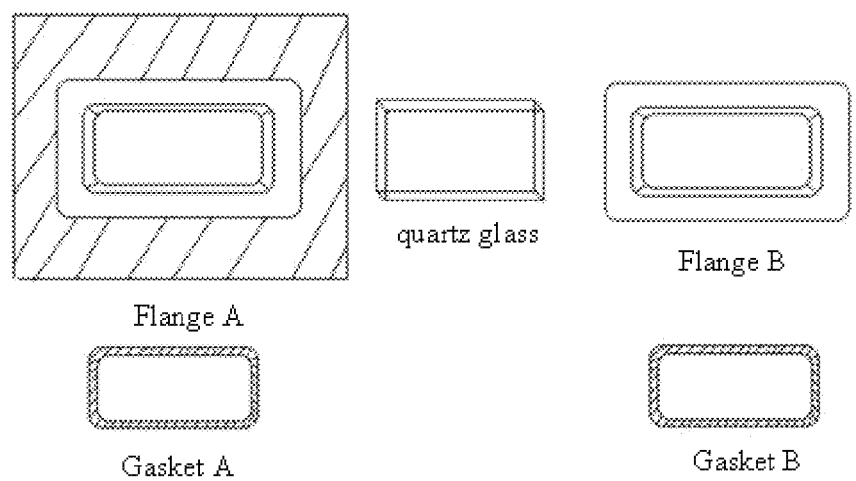
FIG. 6 is a structure schematic diagram of a microwave feed aperture of the microwave fast-evaporation chamber.
Figure 7:
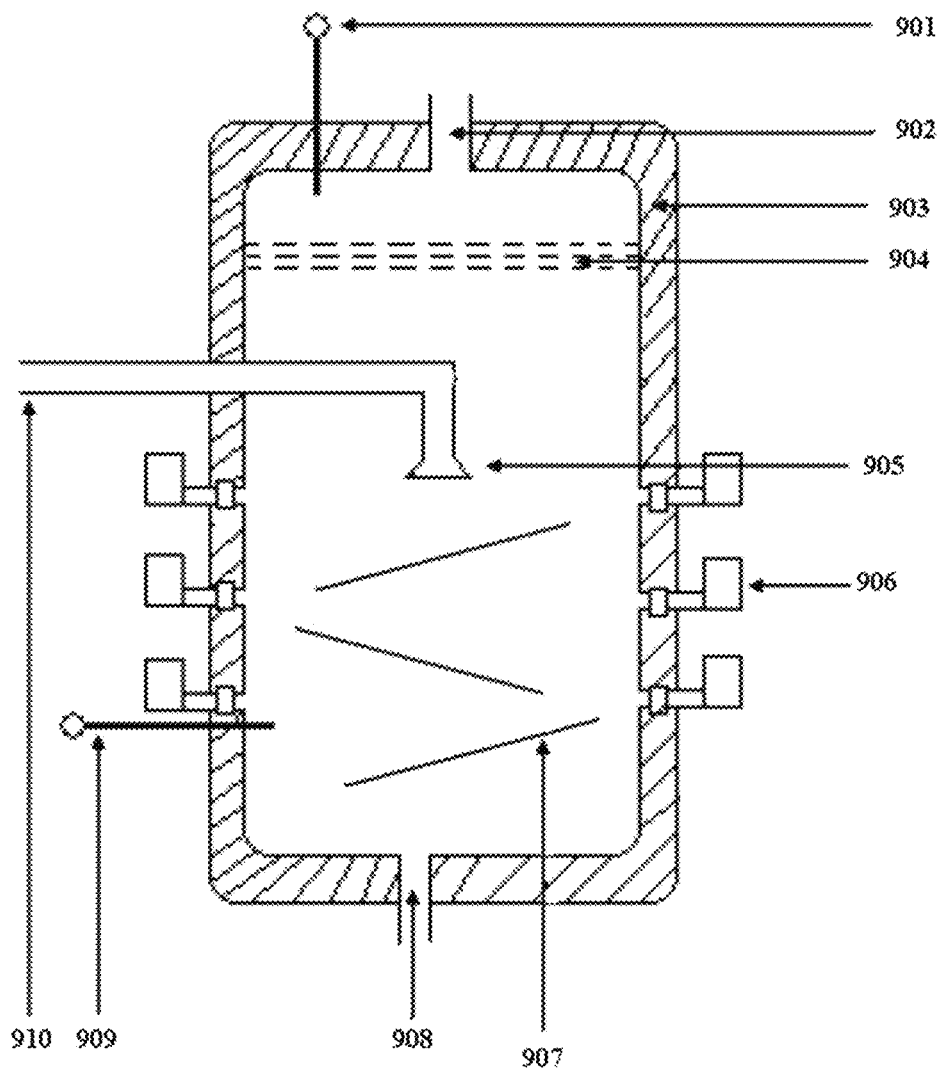
FIG. 7 is a structure schematic diagram of a microwave efficient-evaporation chamber of the invention.
Figure 8:
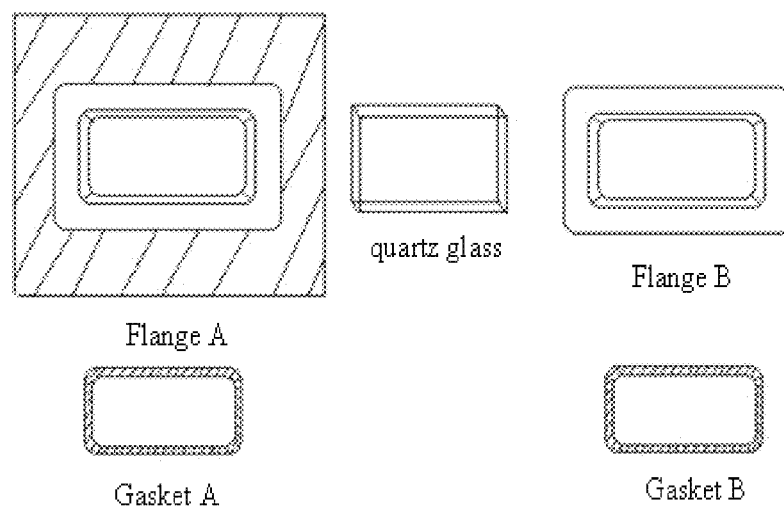
FIG. 8 is a structure schematic diagram of a microwave feed aperture of the microwave efficient-evaporation chamber of the invention.
Figure 9:
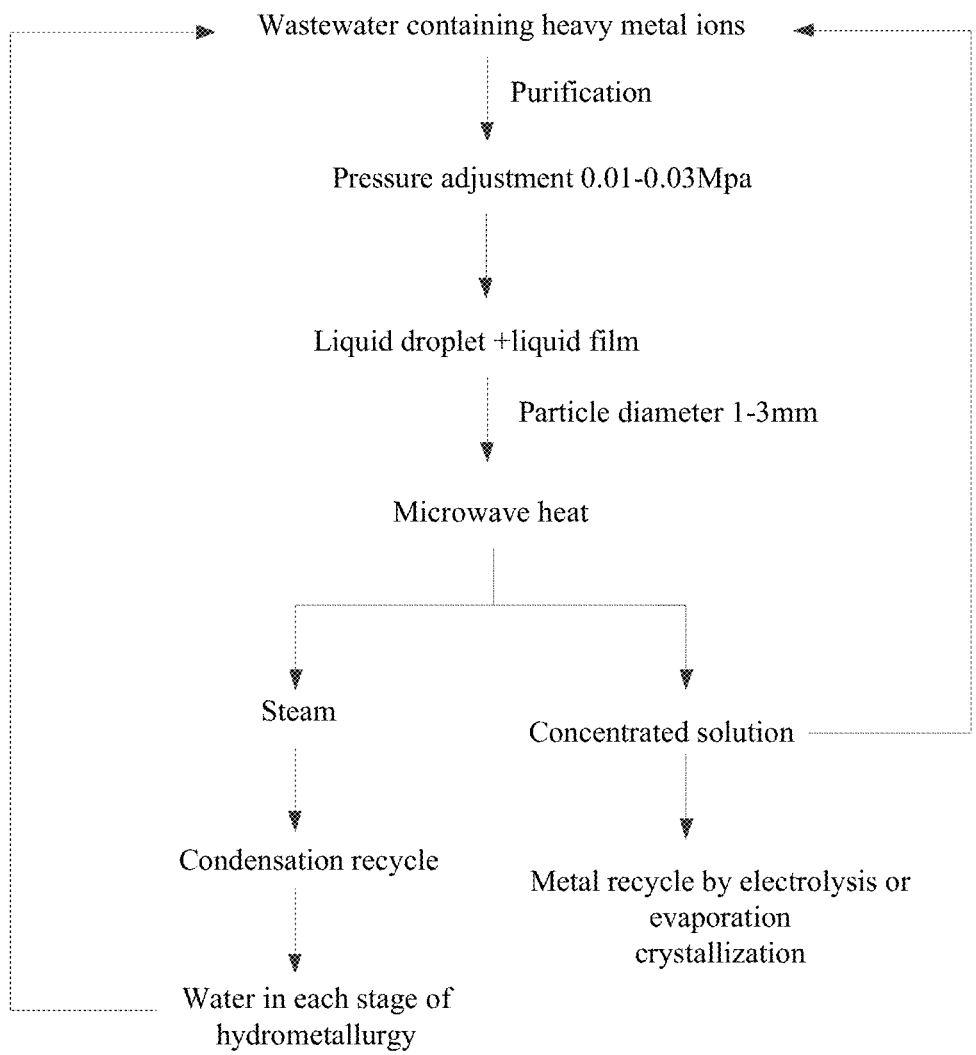
FIG. 9 is a schematic flow chart of effluent disposal of the invention.

As shown in FIG. 1 and FIG. 2, the microwave-evaporation apparatus comprises a feed tank 1, a liquid droplet production unit, a microwave-evaporation unit and an evaporated water recycle unit. The liquid droplet production unit comprises a feed pump 2, a control valve 11 and a high pressure spray head 12. The microwave-evaporation unit comprises a magnetron 3, a demister 4, a thermocouple 5, a steam outlet 6, an evaporation tank 7, a control valve, a discharging pump 13, an evaporation bed 14, a solution outlet 15, a rotary shaft 16, a bearing 17 and a sealing ring 18. The evaporated water recycle unit comprises a steam condenser 8, a distilled water collection tank 9, and a vacuum pump 10. An outlet of the feed tank 1 is connected to the feed pump 2, the control valve and a high press spray head 12 successively by means of pipes. The spray head 12 is inserted into the evaporation tank 7 from a lateral side of the evaporation tank 7 by means of a pipe and is located at a top position inside the evaporation tank 7. A plurality of magnetrons 3 are provided uniformly outside and around the evaporation tank 7. According to the actual conditions, a plurality of thermocouples 5 are provided on the evaporation tank 7. The evaporation bed 14 is provided just below the spray head 12 inside the evaporation tank 7 by means of the rotary shaft 16, the bearing 17 and the sealing ring 18, and the evaporation bed 14 is adjusted within a range of 0° to 90° by the rotary shaft 16. The solution outlet 15 is provided at a bottom portion of evaporation tank 7, and is connect to two pipes, and one of the pipes is directly connected to a control valve, and the other of the pipes is connected back to the spray head 12 by a control valve. The demister 4 is provided at a top position inside the evaporation tank 7. The steam outlet 6 is provided at a top portion of evaporation tank 7, and is connect to the steam condenser 8, the distilled water collection tank 9 and the vacuum pump 10 successively by means of pipes.

A thermal insulation layer is provided between the evaporation chamber 7 and the magnetron 3. The high pressure spray head 12 is made from a reinforced plastic of modified Polytetrafluoroethylene (PTFE), which has excellent temperature resistance (−200° C. to +260° C.), corrosion resistance, aging resistance, Hydrophobic stickiness resistance and machine processability. Moreover, the PTFE is a transparent material which substantively doesn't absorb the microwave so as to ensure the uniform distribution of the microwave inside the evaporation chamber under multi-mode radiation. The evaporation bed 14 is made from silicon carbide wave-absorbing ceramic material.

The microwave flash evaporation apparatus is used for performing seawater evaporation and concentration, and the seawater evaporation and concentration process comprises the following steps:

Step 1: pressure adjustment: adjusting pressure of the evaporation chamber and the steam condenser to be 0.01 MPa by the vacuum pump 10;

Step 2: droplet formation: putting the seawater having a volume of 30 L into the feed tank 1, then passing the seawater through the feed pump 2, the high pressure spray head 12 and then into the evaporation chamber 7 so as to form droplet having diameter of 1 mm;

Step 3: liquid film formation: the droplet forming a liquid film when arriving an evaporation bed 14 in the evaporation chamber 7, wherein the evaporation bed 14 is inclined with respect to a horizontal direction by an angle of 0 degree;

Step 4: microwave evaporation: at the same time as steps 2 and 3, turning on magnetrons 3 of the evaporation chamber 7 so as to heat the droplet and the liquid film in the evaporation chamber 7 by the microwave and at the same time indirectly heat the liquid film and the whole evaporation chamber 7 by the microwave energy absorbed by the evaporation bed to obtain steam, wherein the power of microwave is 800 W, and the frequency thereof is 2.45 GHz; and Step 5: product collection: after passing through the demister 4, the steam obtained in step 4 escaping quickly from the evaporation chamber 7 due to a negative pressure and then going into the stem condenser 8 to be condensate, and collecting distilled water with a volume of 20.1 L by the collection tank 9 and obtaining concentrated seawater.

The application process of solution outlet 15 is as follows: open the feed pump 2 during evaporation process, shut off the discharge pump 13, and at the same time, open valve 11*a*, and shut off valves 11*b* and 11*c*. After the liquid in feed tank 1 are totally evaporated and concentrated by microwave, close the microwave source 3, the vacuum pump 10 and the feed pump 2, and release the vacuum of total system until the pressure in the system reaches the constant pressure, open discharge pump 13, and the concentrated solution is collected through the solution outlet 15.

Example 11

As shown in FIG. 1 and FIG. 2, the microwave-evaporation apparatus comprises a feed tank 1, a liquid droplet production unit, a microwave-evaporation unit and an evaporated water recycle unit. The liquid droplet production unit comprises a feed pump 2, a control valve 11 and a high pressure spray head 12. The microwave-evaporation unit comprises a magnetron 3, a demister 4, a thermocouple 5, a steam outlet 6, an evaporation tank 7, a control valve, a discharging pump 13, an evaporation bed 14, a solution outlet 15, a rotary shaft 16, a bearing 17 and a sealing ring 18. The evaporated water recycle unit comprises a steam condenser 8, a distilled water collection tank 9, and a vacuum pump 10. An outlet of the feed tank 1 is connected to the feed pump 2, the control valve and a high press spray head 12 successively by means of pipes. The spray head 12 is inserted into the evaporation tank 7 from a lateral side of the evaporation tank 7 by means of a pipe and is located at a top position inside the evaporation tank 7. A plurality of magnetrons 3 are provided uniformly outside and around the evaporation tank 7. According to the actual conditions, a plurality of thermocouples 5 are provided on the evaporation tank 7. The evaporation bed 14 is provided just below the spray head 12 inside the evaporation tank 7 by means of the rotary shaft 16, the bearing 17 and the sealing ring 18, and the evaporation bed 14 is adjusted within a range of 0° to 90° by the rotary shaft 16. The solution outlet 15 is provided at a bottom portion of evaporation tank 7, and is connect to two pipes, and one of the pipes is directly connected to a control valve, and the other of the pipes is connected back to the spray head 12 by a control valve. The demister 4 is provided at a top position inside the evaporation tank 7. The steam outlet 6 is provided at a top portion of evaporation tank 7, and is connect to the steam condenser 8, the distilled water collection tank 9 and the vacuum pump 10 successively by means of pipes.

A thermal insulation layer is provided between the evaporation chamber 7 and the magnetron 3. The high pressure spray head 12 is made from a reinforced plastic of modified Polytetrafluoroethylene (PTFE), which has excellent temperature resistance (−200° C. to +260° C.), corrosion resistance, aging resistance, Hydrophobic stickiness resistance and machine processability. Moreover, the PTFE is a transparent material which substantively doesn't absorb the microwave so as to ensure the uniform distribution of the microwave inside the evaporation chamber under multimode radiation. The evaporation bed 14 is made from silicon carbide wave-absorbing ceramic material.

The microwave flash evaporation apparatus is used for performing evaporation and concentration of the spent liquor of Bayer process, and the evaporation and concentration process of the spent liquor of Bayer process comprises the following steps:

Step 1: pressure adjustment: adjusting pressure of the evaporation chamber and the steam condenser to be 0.03 MPa by the vacuum pump 10;

Step 2: droplet formation: putting the spent liquor of Bayer process having a volume of 30 L into the feed tank 1, then passing the spent liquor of Bayer process through the feed pump 2, the high pressure spray head 12 and then into the evaporation chamber 7 so as to form droplet having diameter of 3 mm;

Step 3: liquid film formation: the droplet forming a liquid film when arriving an evaporation bed 14 in the evaporation chamber 7, wherein the evaporation bed 14 is inclined with respect to a horizontal direction by an angle of 90 degree;

Step 4: microwave evaporation: at the same time as steps 2 and 3, turning on magnetrons 3 of the evaporation chamber 7 so as to heat the droplet and the liquid film in the evaporation chamber 7 by the microwave and at the same time indirectly heat the liquid film and the whole evaporation chamber 7 by the microwave energy absorbed by the evaporation bed to obtain steam, wherein the power of microwave is 1200 W, and the frequency thereof is 2.45 GHz; and Step 5: product collection: after passing through the demister 4, the steam obtained in step 4 escaping quickly from the evaporation chamber 7 due to a negative pressure and then going into the stem condenser 8 to be condensate, and collecting distilled water with a volume of 18.8 L by the collection tank 9 and obtaining concentrated spent liquor of Bayer process.

The application process of solution outlet 15 is as follows: open the feed pump 2 during evaporation process, shut off the discharge pump 13, and at the same time, open valve 11a, and shut off valves 11b and 11c. After the liquid in feed tank 1 are totally evaporated and concentrated by microwave, close the microwave source 3, the vacuum pump 10 and the feed pump 2, and release the vacuum of total system until the pressure in the system reaches the constant pressure, open discharge pump 13, and the concentrated solution is collected through the solution outlet 15.

Example 12

As shown in FIG. 1 and FIG. 2, the microwave-evaporation apparatus comprises a feed tank 1, a liquid droplet production unit, a microwave-evaporation unit and an evaporated water recycle unit. The liquid droplet production unit comprises a feed pump 2, a control valve 11 and a high pressure spray head 12. The microwave-evaporation unit comprises a magnetron 3, a demister 4, a thermocouple 5, a steam outlet 6, an evaporation tank 7, a control valve, a discharging pump 13, an evaporation bed 14, a solution outlet 15, a rotary shaft 16, a bearing 17 and a sealing ring 18. The evaporated water recycle unit comprises a steam condenser 8, a distilled water collection tank 9, and a vacuum pump 10. An outlet of the feed tank 1 is connected to the feed pump 2, the control valve and a high press spray head 12 successively by means of pipes. The spray head 12 is inserted into the evaporation tank 7 from a lateral side of the evaporation tank 7 by means of a pipe and is located at a top position inside the evaporation tank 7. A plurality of magnetrons 3 are provided uniformly outside and around the evaporation tank 7. According to the actual conditions, a plurality of thermocouples 5 are provided on the evaporation tank 7. The evaporation bed 14 is provided just below the spray head 12 inside the evaporation tank 7 by means of the rotary shaft 16, the bearing 17 and the sealing ring 18, and the evaporation bed 14 is adjusted within a range of 0° to 90° by the rotary shaft 16. The solution outlet 15 is provided at a bottom portion of evaporation tank 7, and is connect to two pipes, and one of the pipes is directly connected to a control valve, and the other of the pipes is connected back to the spray head 12 by a control valve. The demister 4 is provided at a top position inside the evaporation tank 7. The steam outlet 6 is provided at a top portion of evaporation tank 7, and is connect to the steam condenser 8, the distilled water collection tank 9 and the vacuum pump 10 successively by means of pipes.

A thermal insulation layer is provided between the evaporation chamber 7 and the magnetron 3. The high pressure spray head 12 is made from a reinforced plastic of modified Polytetrafluoroethylene (PTFE), which has excellent temperature resistance (−200° C. to +260° C.), corrosion resistance, aging resistance, Hydrophobic stickiness resistance and machine processability. Moreover, the PTFE is a transparent material which substantively doesn't absorb the microwave so as to ensure the uniform distribution of the microwave inside the evaporation chamber under multi-mode radiation. The evaporation bed 14 is made from silicon carbide wave-absorbing ceramic material.

The microwave flash evaporation apparatus is used for performing seawater evaporation and concentration, and the seawater evaporation and concentration process comprises the following steps:

Step 1: pressure adjustment: adjusting pressure of the evaporation chamber and the steam condenser to be 0.02 MPa by the vacuum pump 10;

Step 2: droplet formation: putting the seawater having a volume of 30 L into the feed tank 1, then passing the seawater through the feed pump 2, the high pressure spray head 12 and then into the evaporation chamber 7 so as to form droplet having diameter of 2 mm;

Step 3: liquid film formation: the droplet forming a liquid film when arriving an evaporation bed 14 in the evaporation chamber 7, wherein the evaporation bed 14 is inclined with respect to a horizontal direction by an angle of 10 degree;

Step 4: microwave evaporation: at the same time as steps 2 and 3, turning on magnetrons 3 of the evaporation chamber 7 so as to heat the droplet and the liquid film in the evaporation chamber 7 by the microwave and at the same time indirectly heat the liquid film and the whole evaporation chamber 7 by the microwave energy absorbed by the evaporation bed to obtain steam, wherein the power of microwave is 1200 W, and the frequency thereof is 2.45 GHz; and Step 5: product collection: after passing through the demister 4, the steam obtained in step 4 escaping quickly from the evaporation chamber 7 due to a negative pressure and then going into the stem condenser 8 to be condensate, and collecting distilled water with a volume of 26.7 L by the collection tank 9 and obtaining concentrated seawater.

The application process of solution outlet 15 is as follows: open the feed pump 2 during evaporation process, shut off the discharge pump 13, and at the same time, open valve 11a, and shut off valves 11b and 11c. After the liquid in feed tank 1 are totally evaporated and concentrated by microwave, close the microwave source 3, the vacuum pump 10 and the feed pump 2, and release the vacuum of total system until the pressure in the system reaches the constant pressure, open discharge pump 13, and the concentrated solution is collected through the solution outlet 15.

Example 13

The microwave flash evaporation apparatus is used for performing sterilization of orange juice put into the feed tank and the sterilization process comprises the following steps:

Step 1: primary microwave sterilization: heating liquid up to a temperature of 50° C. in a primary microwave sterilization chamber and sterilizing for a time of 10 min;

Step 2: secondary microwave sterilization: after the first sterilization, performing secondary microwave sterilization;

1) pressure adjustment: adjusting pressure of a sterilization chamber to be 0.27 MPa by a pressure regulating valve and sterile air;

2) Liquid spray: after finishing the step 1), passing the liquid containing bacterium through a feed pump, a high pressure spray head and then into the sterilization chamber so as to form droplet having a diameter of 1 mm and a shape of reversed cone and uniformly distributed in the sterilization chamber; and 3) high temperature sterilization: at the same time as step 2, turning on a microwave source around the sterilization chamber so as to directly heat the droplet in the sterilization chamber by the microwave, and quickly perform sterilization by thermal effect and non-thermal effect of microwave, wherein the temperature of the sterilization chamber is control to be 130° C., and the sterilization time for the secondary sterilization is kept to be 1.5 s; and Step 3: product collection: collecting the liquid after microwave sterilization by a collecting tank.

Liquid after the microwave sterilization can be stored at room temperature, and the shelf life thereof is up to 6 months or more.

Example 14

The microwave flash evaporation apparatus is used for performing sterilization of orange juice put into the feed tank and the sterilization process comprises the following steps:

Step 1: primary microwave sterilization: heating liquid up to a temperature of 95° C. in a primary microwave sterilization chamber and sterilizing for a time of 1 min;

Step 2: secondary microwave sterilization: after the first sterilization, performing secondary microwave sterilization;

1) pressure adjustment: adjusting pressure of a sterilization chamber to be 0.36 MPa by a pressure regulating valve and sterile air;

2) Liquid spray: after finishing the step 1), passing the liquid containing bacterium through a feed pump, a high pressure spray head and then into the sterilization chamber so as to form droplet having diameter of 3 mm and uniformly distributed in the sterilization chamber; and 3) high temperature sterilization: at the same time as step 2, turning on a microwave source around the sterilization chamber so as to directly heat the droplet in the sterilization chamber by the microwave, and quickly perform sterilization by thermal effect and non-thermal effect of microwave, wherein the temperature of the sterilization chamber is control to be 140° C., and the sterilization time for the secondary sterilization is kept to be 0.5 s; and Step 3: product collection: collecting the liquid after microwave sterilization by a collecting tank.

Liquid after the microwave sterilization can be stored at room temperature, and the shelf life thereof is up to 6 months or more.

Example 15

The microwave flash evaporation apparatus is used for performing sterilization of Green tea put into the feed tank and the sterilization process comprises the following steps:

Step 1: primary microwave sterilization: heating liquid up to a temperature of 80° C. in a primary microwave sterilization chamber and sterilizing for a time of 10 min;

Step 2: secondary microwave sterilization: after the first sterilization, performing secondary microwave sterilization;

1) pressure adjustment: adjusting pressure of a sterilization chamber to be 0.31 MPa by a pressure regulating valve and sterile air;

2) Liquid spray: after finishing the step 1), passing the liquid containing bacterium through a feed pump, a high pressure spray head and then into the sterilization chamber so as to form droplet having diameter of 2 mm and uniformly distributed in the sterilization chamber; and 3) high temperature sterilization: at the same time as step 2, turning on a microwave source around the sterilization chamber so as to directly heat the droplet in the sterilization chamber by the microwave, and quickly perform sterilization by thermal effect and non-thermal effect of microwave, wherein the temperature of the sterilization chamber is control to be 135° C., and the sterilization time for the secondary sterilization is kept to be 0.8 s; and Step 3: product collection: collecting the liquid after microwave sterilization by a collecting tank.

Liquid after the microwave sterilization can be stored at room temperature, and the shelf life thereof is up to 6 months or more.

Example 16

The microwave flash evaporation apparatus is used for performing sterilization of green tea put into the feed tank and the sterilization process comprises the following steps:

Step 1: primary microwave sterilization: heating liquid up to a temperature of 60° C. in a primary microwave sterilization chamber and sterilizing for a time of 6 min;

Step 2: secondary microwave sterilization: after the first sterilization, performing secondary microwave sterilization;

1) pressure adjustment: adjusting pressure of a sterilization chamber to be 0.3 MPa by a pressure regulating valve and sterile air;

2) Liquid spray: after finishing the step 1), passing the liquid containing bacterium through a feed pump, a high pressure spray head and then into the sterilization chamber so as to form droplet having diameter of 2 mm and uniformly distributed in the sterilization chamber; and 3) high temperature sterilization: at the same time as step 2, turning on a microwave source around the sterilization chamber so as to directly heat the droplet in the sterilization chamber by the microwave, and quickly perform sterilization by thermal effect and non-thermal effect of microwave, wherein the temperature of the sterilization chamber is control to be 138° C., and the sterilization time for the secondary sterilization is kept to be 1 s; and Step 3: product collection: collecting the liquid after microwave sterilization by a collecting tank.

Liquid after the microwave sterilization can be stored at room temperature, and the shelf life thereof is up to 5 months or more.

What is claimed is:

1. A microwave flash evaporation apparatus, wherein said microwave flash evaporation apparatus is a microwave-evaporation apparatus, the microwave flash evaporation apparatus comprising:
   a feed tank,
   a liquid droplet production unit,
   a microwave-evaporation unit, and
   an evaporated water recycle unit,
   wherein the liquid droplet production unit comprises a feed pump, a first control valve and a high pressure spray head;
   the microwave-evaporation unit comprises a plurality of magnetrons, a demister, a thermocouple, a steam outlet, an evaporation tank, a second control valve, a third control valve, a discharging pump, an evaporation bed, a solution outlet, a rotary shaft, a bearing and a sealing ring; and
   the evaporated water recycle unit comprises a steam condenser, a distilled water collection tank, and a vacuum pump,
   wherein an outlet of the feed tank is connected to the feed pump, the first control valve, a high press spray head successively through pipes;
   the spray head is inserted into the evaporation tank from a lateral side of the evaporation tank through a pipe and is located at a top position inside the evaporation tank;
   the plurality of magnetrons are provided uniformly outside and around the evaporation tank;
   a plurality of thermocouples are provided on the evaporation tank;
   the evaporation bed is provided just below the spray head inside the evaporation tank the rotary shaft, the bearing and the sealing ring, and the evaporation bed is adjusted within a range of 0° to 90° by the rotary shaft;
   the solution outlet is provided at a bottom portion of evaporation tank, and is connected to two pipes, one of the pipes being directly connected to the third control valve, and the other of the pipes being connected back to the spray head by the second control valve;
   the demister is provided at a top position inside the evaporation tank;
   the steam outlet is provided at a top portion of evaporation tank, and is connected to the steam condenser, the distilled water collection tank and the vacuum pump successively through of pipes.

2. The microwave flash evaporation apparatus according to claim 1, wherein a thermal insulation layer is provided between the evaporation tank and the magnetrons, and the thermal insulation layer is selected from thermal insulation cotton, insulation mud and thermal insulation brick.

3. The microwave flash evaporation apparatus according to claim 1, wherein the high pressure spray head is made from a reinforced plastic of modified Polytetrafluoroethylene (PTFE); and
   the evaporation bed is made from carborundum, Silicon nitride, aluminum oxide, barium tatanate, clay soil or Wave-absorbing carbon black ceramic materials.

4. The microwave flash evaporation apparatus according to claim 3, wherein the evaporation bed comprises a plurality of evaporation beds disposed above one another in the vertical direction.

5. The microwave flash evaporation apparatus according to claim 1, wherein the evaporation tank is selected from a microwave-enhanced evaporation chamber, a microwave fast-evaporation chamber and a microwave efficient-evaporation chamber.

6. The microwave flash evaporation apparatus according to claim 5, wherein the microwave-enhanced evaporation chamber comprises an evaporation cell, a microwave source, an inlet of solution to be concentrated, a steam outlet, a concentrated solution outlet, a demister and a high pressure spray head,
   wherein the microwave source is provided at the evaporation cell;
   one end of evaporation cell is provided with the steam outlet the demister, the inlet of solution to be concentrated and the high pressure spray head, and the other end of the evaporation cell is provided with the concentrated solution outlet;
   a thermal insulation layer is provided at an outer-wall of the evaporation cell;
   thermocouples are provided at an end where the steam outlet of the evaporation cell is located and an end where the concentrated solution outlet of the evaporation cell is located, connected to a microwave generator, and controlled by Micro Controller Unit (MCU) so as to adjust power of microwave in real time; and
   the steam outlet is connected to a vacuum apparatus so as to enhance evaporation.

7. The microwave flash evaporation apparatus according to claim 6, wherein an inner-wall material of the evaporation cell is made from a corrosion-resistant stainless steel, and is acted as a multimode reflector under radiation of microwave so as to make solution to be heated quickly, boiled, evaporated, and then concentrated.

8. The microwave flash evaporation apparatus according to any one of claim 6, wherein the microwave source is provided from the end where the concentrated solution outlet of the evaporation cell is located to a middle position of the evaporation cell, and the microwave is fed into the evaporation cell through a microwave feed aperture of the evaporation cell so as to provide energy required by evaporation; and
   the microwave feed aperture is made from stainless steel flange, glass cement, Polytetrafluoroethylene gasket or quartz glass, and seal strength of the microwave feed aperture is within a range of −0.1 MPa to 1 MPa and is up to 1 MPa.

9. The microwave flash evaporation apparatus according to claim 5, wherein the microwave fast-evaporation chamber includes a steam temperature meter, a steam outlet, a thermal insulation layer, a solution inlet, a microwave source, sieve plate evaporation beds, a droplet dispersion porous plate, a solution outlet, a demister, a concentrated solution temperature meter,
   Wherein the thermal insulation layer is provided at an outer-wall of the evaporation chamber;
   the microwave source is provided on the evaporation chamber;
   one end of the evaporation chamber is provided with the steam outlet, the steam temperature meter, the demister and the solution inlet, and the other end of the evaporation chamber is provided with the solution outlet, and the concentrated solution temperature meter; and
   the sieve plate evaporation beds and the droplet dispersion porous plate are provided successively between an end where the solution outlet is located and a middle portion of the evaporation chamber; and
   the microwave source is provided between the end where the solution outlet of the evaporation chamber is located and the middle portion of the evaporation chamber, and the microwave is fed into the evaporation chamber through a microwave feed aperture of the evaporation chamber so as to provide energy required by evaporation.

10. The microwave flash evaporation apparatus according to claim 9, wherein an inner-wall of the evaporation chamber is made from stainless steel, and after optimization design of the position of a microwave feed aperture and feeding microwave, the inner-wall of the evaporation chamber forms a multimode resonant cavity so as to make solution to be heated quickly, boiled, evaporated and then concentrated; and the microwave feed aperture is made from stainless steel flange, Polytetrafluoroethylene, silicone gaskets or quartz glass.

11. The microwave flash evaporation apparatus according to claim 9, wherein a material for making the sieve plate evaporation beds is wave-absorbing ceramics, and a pore diameter of the sieve plate evaporation beds is in the range of 0.1 mm to 20 mm; and a material for making the droplet dispersion porous plate is wave-non-absorbing ceramics, and a pore diameter of the droplet dispersion porous plate is in the range of 0.1 mm to 20 mm.

12. The microwave flash evaporation apparatus according to claim 5, wherein microwave efficient-evaporation chamber comprises a steam temperature meter, a steam outlet, a thermal insulation layer, a demister, a high pressure spray head, a microwave source, evaporation beds, a solution outlet, a concentrated solution temperature meter, and a solution inlet;

Wherein the thermal insulation layer is provided at an outer-wall of the evaporation chamber;

the microwave source is provided on the evaporation chamber;

one end of the evaporation chamber is provided with the steam outlet, the steam temperature meter, the demister and the solution inlet, and an end of the solution inlet being provided with the spray head;

the other end of the evaporation chamber is provided with the solution outlet, and the concentrated solution temperature meter; and the evaporation beds are provided between an end where the solution outlet is located and a middle portion of the evaporation chamber;

the steam outlet is connected to a vacuum apparatus so as to enhance evaporation; and the microwave source is provided between the end where the solution outlet of the evaporation chamber is located and the middle portion of the evaporation chamber, and the microwave is fed into the evaporation chamber through a microwave feed aperture of the evaporation chamber so as to provide energy required by evaporation.

13. The microwave flash evaporation apparatus according to claim 12, wherein an inner-wall of the evaporation chamber is made from stainless steel, and after optimization of the position and number of a microwave feed aperture, under the microwave, the inner-wall of the evaporation chamber forms a multi-mode resonant cavity so as to make solution to be heated quickly, boiled, evaporated and then concentrated; and the microwave feed aperture is made from stainless steel flange, glass cement, Polytetrafluoroethylene gasket or quartz glass, seal strength of the microwave feed aperture is within a range of −0.1 MPa to 1 MPa and is up to 1 MPa.

14. The microwave flash evaporation apparatus according to claim 1, further comprising a purifier disposed in the feed tank.

15. A method for treating wastewater containing heavy metal ions by using the microwave flash evaporation apparatus according to claim 1, wherein the microwave flash evaporation apparatus is a microwave-evaporation apparatus and comprises a feed tank, a liquid droplet production unit, a microwave-evaporation unit and an evaporated water recycle unit, wherein the liquid droplet production unit comprises a feed pump, a first control valve and a high pressure spray head;

the microwave-evaporation unit comprises a plurality of magnetrons, a demister, a thermocouple, a steam outlet, an evaporation tank, a second control valve, a third control valve, a discharging pump, an evaporation bed, a solution outlet, a rotary shaft, a bearing and a sealing ring; and the evaporated water recycle unit comprises a steam condenser, a distilled water collection tank, and a vacuum pump, wherein an outlet of the feed tank is connected to the feed pump, the first control valve, a high press spray head successively through pipes;

the spray head is inserted into the evaporation tank from a lateral side of the evaporation tank through a pipe and is located at a top position inside the evaporation tank;

the plurality of magnetrons are provided uniformly outside and around the evaporation tank;

a plurality of thermocouples are provided on the evaporation tank;

the evaporation bed is provided just below the spray head inside the evaporation tank through the rotary shaft, the bearing and the sealing ring, and the evaporation bed is adjusted within a range of 0° to 90° by the rotary shaft;

the solution outlet is provided at a bottom portion of evaporation tank, and is connected to two pipes, one of the pipes being directly connected to the third control valve, and the other of the pipes being connected back to the spray head by the second control valve;

the demister is provided at a top position inside the evaporation tank;

the steam outlet is provided at a top portion of evaporation tank, and is connected to the steam condenser, the distilled water collection tank and the vacuum pump successively through pipes; and the method comprising:

Step 1: pressure adjustment: adjusting pressures of the evaporation tank and the steam condenser to be between 0.01 MPa and 0.03 Mpa by the vacuum pump;

Step 2: purification: putting the wastewater containing heavy metal ions into the feed tank, and removing big particle or agglomeration type impurity from wastewater containing heavy metal ions in the feed tank;

Step 3: droplet and liquid film formation: passing the wastewater containing heavy metal ions through the feed pump, the high pressure spray head and then into the evaporation tank so as to form droplets having a diameter in a range of 1 mm to 3 mm, the droplets then absorbing the microwave energy so as to concentrate during falling, and forming liquid film and droplet when arriving the evaporation bed in the evaporation tank;

Step 4: microwave evaporation: at the same time as step 3, turning on the magnetrons outside the evaporation tank so as to directly heat the droplet and liquid film in the evaporation tank by the microwave and at the same time indirectly heat the liquid film and the whole evaporation magnetrons by the microwave energy absorbed by the evaporation bed to obtain steam;

Step 5: product collection: after passing through the demister, the steam obtained in step 4 escaping quickly from the evaporation tank due to a negative pressure and then going into the stem condenser to be condensate, and collecting distilled water by the collection tank and obtaining concentrated solution containing heavy metal ions; and Step 6: product recycle: using the distilled water as dilution water in each stage of hydrometallurgy and wash water of boiler, directly returning the concentrated solution containing heavy metal ions to be electrolyzed so as to recycle metal ions, and recycling the metal ions in a form of hydroxide or carbonate of these heavy metal ions by using alkali to neutralize and precipitate, or recycling the metal ions in a form of metal salt crystal by secondary microwave evaporation crystallization.

16. A method for performing evaporation concentration of spent liquor of Bayer by using the microwave flash evaporation apparatus according to claim 1, wherein the microwave flash evaporation apparatus is a microwave-evaporation apparatus and comprises a feed tank, a liquid droplet production unit, a microwave-evaporation unit and an evaporated water recycle unit, wherein the liquid droplet production unit comprises a feed pump, a first control valve and a high pressure spray head;

the microwave-evaporation unit comprises a plurality of magnetrons, a demister, a thermocouple, a steam outlet, an evaporation tank, a second control valve, a third control valve, a discharging pump, an evaporation bed, a solution outlet, a rotary shaft, a bearing and a sealing ring; and the evaporated water recycle unit comprises a steam condenser, a distilled water collection tank, and a vacuum pump, wherein an outlet of the feed tank is connected to the feed pump, the first control valve, a high press spray head successively through pipes;

the spray head is inserted into the evaporation tank from a lateral side of the evaporation tank through a pipe and is located at a top position inside the evaporation tank;

the plurality of magnetrons are provided uniformly outside and around the evaporation tank;

a plurality of thermocouples are provided on the evaporation tank;

the evaporation bed is provided just below the spray head inside the evaporation tank through the rotary shaft, the bearing and the sealing ring, and the evaporation bed is adjusted within a range of 0° to 90° by the rotary shaft;

the solution outlet is provided at a bottom portion of evaporation tank, and is connected to two pipes, one of the pipes being directly connected to the third control valve, and the other of the pipes being connected back to the spray head by the second control valve;

the demister is provided at a top position inside the evaporation tank;

the steam outlet is provided at a top portion of evaporation tank, and is connected to the steam condenser, the distilled water collection tank and the vacuum pump successively through pipes; and the method comprising:

Step 1: pressure adjustment: adjusting pressure of the evaporation tank and the steam condenser to be between 0.01 MPa and 0.03 Mpa by the vacuum pump;

Step 2: droplet formation: putting the spent liquor of Bayer process into the feed tank, then passing the spent liquor of Bayer process through the feed pump, the high pressure spray head and then into the evaporation tank so as to form droplet having a diameter in a range of 1 mm to 3 mm;

Step 3: liquid film formation: the droplet forming a liquid film when arriving the evaporation bed in the evaporation tank;

Step 4: microwave evaporation: at the same time as steps 2 and 3, turning on the magnetrons around the evaporation tank so as to heat the droplet and the liquid film in the evaporation tank by the microwave and at the same time indirectly heat the liquid film and the whole evaporation tank by the microwave energy absorbed by the evaporation bed to obtain steam; and Step 5: product collection: after passing through the demister, the steam obtained in step 4 escaping quickly from the evaporation tank due to a negative pressure and then going into the stem condenser to be condensate, and collecting distilled water by the collection tank and obtaining concentrated spent liquor of Bayer process.

* * * * *